US006294518B1

(12) United States Patent
Potter et al.

(10) Patent No.: US 6,294,518 B1
(45) Date of Patent: Sep. 25, 2001

(54) CELL-PERMEABLE PROTEIN INHIBITORS OF CALPAIN

(75) Inventors: David A. Potter, Brighton; Paul Skolnik, Sharon, both of MA (US)

(73) Assignee: New England Medical Center Hospitals, Inc., Boston, MA (US)

( * ) Notice: Subject to any disclaimer, the term of this patent is extended or adjusted under 35 U.S.C. 154(b) by 0 days.

(21) Appl. No.: 09/441,416

(22) Filed: Nov. 16, 1999

Related U.S. Application Data

(63) Continuation-in-part of application No. 08/964,302, filed on Nov. 4, 1997, now Pat. No. 6,015,787.

(51) Int. Cl.[7] .......................... A61K 38/02; A61K 38/55; C07K 14/81
(52) U.S. Cl. ................. 514/12; 514/13; 530/324
(58) Field of Search .................. 514/2.12, 13.21; 530/300, 324, 325, 326, 350

(56) References Cited

U.S. PATENT DOCUMENTS

| | | | |
|---|---|---|---|
| 6,015,787 | * | 1/2000 | Potter et al. ............... 514/12 |
| 6,057,290 | * | 5/2000 | Fukiage et al. ............ 514/12 |

FOREIGN PATENT DOCUMENTS

| | | | |
|---|---|---|---|
| 395309 | * | 10/1990 | (EP) . |
| 95/34295 | * | 12/1995 | (WO) . |

OTHER PUBLICATIONS

Anagli et al., "Investigation of the role of calpain as a stimulus–response mediator in human platelets using new synthetic inhibitors", Biochem. J. 274:497–502, 1991.

Croall et al., "Domain Structure of Calpain: Mapping the Binding Site for Calpastatin", Biochemistry 33:13223–13230, 1994.

Emori et al., "All Four Repeating Domains of the Endogenous Inhibitor for Calcium–dependent Protease . . . " The Journal of Biological Chemistry 263:2364–2370, 1988.

Emori et al., "Endogenous inhibitor for calcium–dependent cysteine protease contains four internal . . ." Proc. Natl. Acad. Sci. USA 84:3590–3594, 1987.

Eto et al., "The Role of the Calpain–Calpastatin System in Thyrotropin–releasing Hormone–induced . . . " The Journal of Biological Chemistry 270:25115–25120, 1995.

Fujise et al., "Specificity of the High Affinity Interaction of Protein Kinase C with a . . ." The Journal of Biological Chemistry 269:31642–31648, 1994.

Hong et al., "Protein kinase C isoforms in muscle cells and their regulation by phorbol ester and calpain", Biochimica et Biophysica Acta 1267:45–54, 1995.

Huang et al., "Ester and Amide Derivatives of E64c as Inhibitors of Platelet Calpains", J. Med. Chem. 35:2048–2054, 1992.

Ishima et al., "Structure of the active 27–residue fragment of human calpastatin", FEBS 294:64–66, 1991.

Kawasaki et al., "Calpastatin Has Two Distinct Sites for Interaction with Calpain—Effect of . . . " Archives of Biochemistry and Biophysics 305:467–472, 1993.

Kawasaki et al., "Identification and Characterization of Inhibitory Seqeunces in Four Repeating . . . " J. Biochem. 106:274–281, 1989.

(List continued on next page.)

*Primary Examiner*—Jeffrey E. Russel
(74) *Attorney, Agent, or Firm*—Fish & Richardson P.C.

(57) ABSTRACT

Fusion proteins have been discovered that contain a calpastatin peptide and a signal sequence capable of delivering the fusion protein into a cell. These proteins can be used to inhibit calpain and, more specifically, to inhibit platelet aggregation or degranulation, to inhibit or reverse erythrocyte sickling, to inhibit a human immunodeficiency virus (HIV), or to inhibit unwanted cellular proliferation or migration.

29 Claims, 14 Drawing Sheets

OTHER PUBLICATIONS

Lin et al., "Inhibition of Nuclear Translocation of Transcription Factor NF–kB by a Synthetic . . ." Journal of Biological Chemistry 270:14255–14258, 1995.

Lin et al., "Role of Nuclear Localization Sequence in Fibroblast Growth Factor–1 . . ." Journal of Biological Chemistry 271:5305–5308, 1996.

Liu et al., "Identification of a functionally import sequence in the cytoplasmic tail of intergrin . . . " Proc. Natl. Adac. Sci. USA 93:11819–11824, 1996.

Ma et al., "Requirement of Different Subdomains of Calpastatin for Calpain Inhibition and for Binding . . . " J. Biochem. 113:591–599, 1993.

Ma et al., "Amino–terminal Conserved Region in Proteinase inhibitor Domain of Calpastatin Potentiates . . ." Journal of Biological Chemistry 269:24430–24436, 1994.

Maki et al., "Inhibition of Calpain by a Synthetic Oligopeptide Corresponding . . . " Journal of Biological Chemistry 264:18866–18869, 1989.

Maki et al., "All four internally repetitive domains of pig calpastatin possess . . . " FEBS 223:174–180, 1987.

Maki et al., "Repetitve Region of Calpastatin is a Functional Unit of the . . . " Biochem. and Biophys. Res. Com. 143:300–308, 1987.

Maki et al., "Analysis of Structure–Function Relationship of Pig Calpastatin . . . " Journal of Biolgcal Chemistry 263:10254–10261, 1988.

McGowan et al., "Inhibition of Calpain in intact platelets by the thiol protease inhibitor . . . " Biochem. and Biophys. Res. Com. 158:432–435, 1989.

Mellgren et al., "The binding of large calpastatin to biologic membranes in mediated in part by . . . " Biochimca et Biophysica Acta 999:71–77, 1989.

Melloni et al., "Modulation of the Calpain Autoproteolysis by Calpastatin And . . . " Biochem. and Biophys. Res. Com. 229:193–197, 1996.

Mohan et al., Purification and Properties of High Molecular Weight Calpastatin . . . Journal of Neurochemistry 64:859–866, 1995.

Prochiantz, A., "Getting hydrophilic compounds into cells: lessons from homeopeptides", Curr. Opinion in Neurobiol. 6:629–634, 1996.

Resing et al., "Independent Reguation of Two Cytoplasmic Processing Stages of the Intermediate . . . " Journal of Biological Chemistry 268:25139–25145, 1993.

Rojas et al., "Controlling Epidermal Growth Factor (EGF-)–stimulated Ras . . . " Journal of Biological Chemistry 271:27456–27461, 1996.

Routtenberg, A., "Measuring Memory in a Mouse Model of Alzheimer's Disease", Science 277:839–840, 1997.

Ryan et al., "Knockout–Transgenic Mouse Model of Sickle Cell Disease", Science 278:873–878, 1997.

Saido et al., "Purification and Characterization of Protein Kinase C from Rabbit Brain", Biochemistry 31:482–490, 1992.

Shea et al., "Enhancement of Neurite Outgrowth Following Calpain Inhibition . . . " Journal of Neurochemistry 65:517–523, 1995.

Takano et al., "Evidence for the repetitive domain structure of pig calpastatin . . . " FEBS 208:199–202, 1986.

Uemori et al., "Characterization of a Functional Domain of Human Calpastatin", Biochem. and Biophys. Res. Com. 166:1485–1493, 1990.

Wang et al., "Development and Therpeutic Potential of Calpain Inhibitors", Adv. Exp. Med. and Biol. 389:118–152, 1990.

Yamazaki et al., "Specific Increase of Amyloid Beta–Protein 42 . . . " Biochemistry 36:8377–8383, 1997.

Yang et al., "Analysis of Calcium–Independent Interaction between Amino–terminal . . . " Journal of Biological Chemistry 269:18977–18984, 1994.

Yano et al., "The Effects of Calpeptin (A Calpain Specific Inhibitor) on an agonist . . . " Thrombosis Research 71:385–395, 1993.

\* cited by examiner

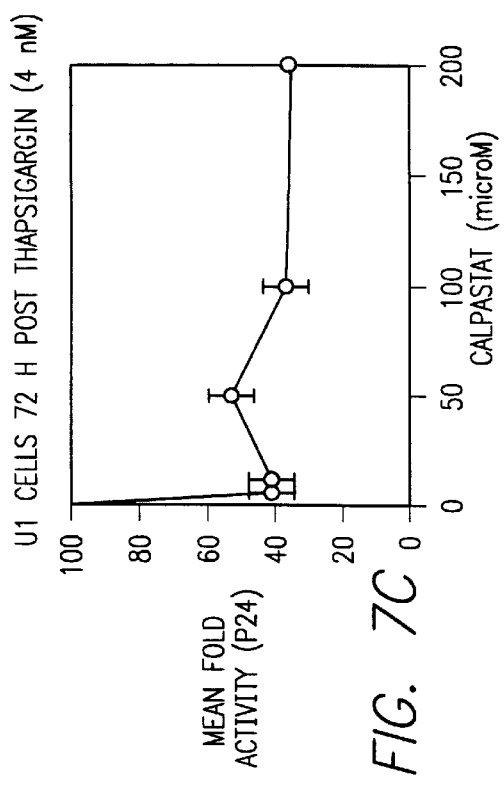
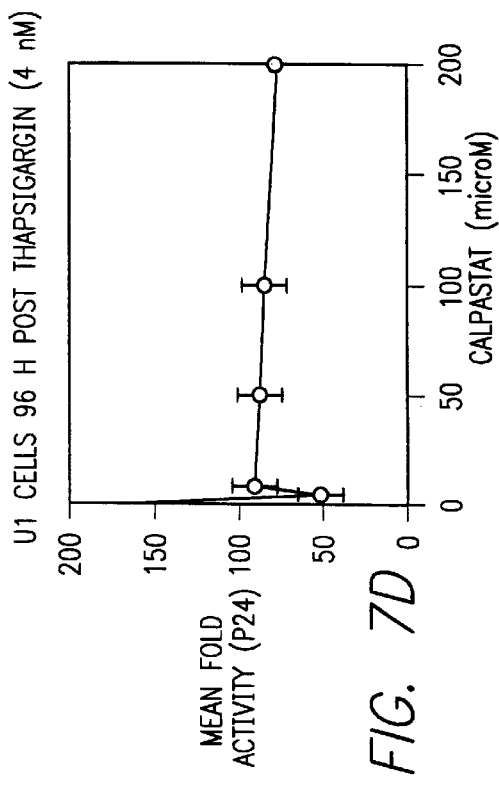
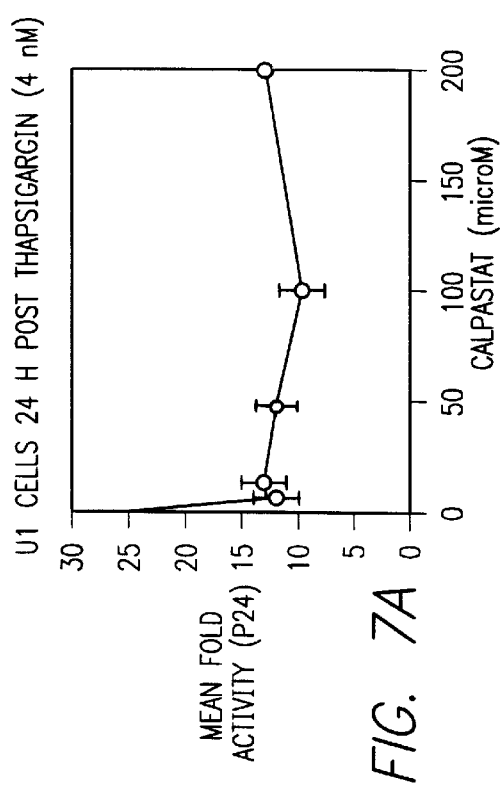
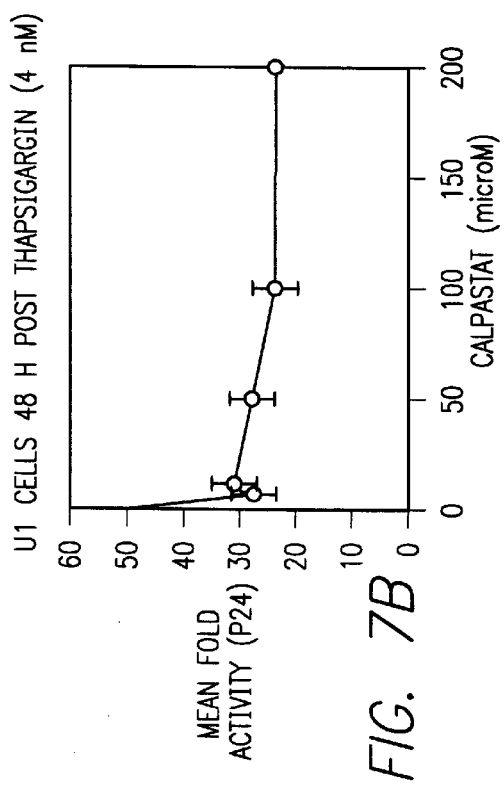
FIG. 7A
FIG. 7B
FIG. 7C
FIG. 7D

○ S-TIPPEYIN
□ S-TIPPEYALA

```
  1 GCCGCC ATG GCC GCG GTA GCG CTG CTC CCG GCG GTC CTG CTG GCC TTG CTG GCG CCC GAA    60
  1        M   A   A   V   A   L   L   P   A   V   L   L   A   L   L   A   P   E     18
 61 AAG CTG GGT GAG AGA GAC GAC ACA ATT CCT CCA GAG TAC AGG GAA CTT CTG GAG AAA AAA  120
 19  K   L   G   E   R   D   D   T   I   P   P   E   Y   R   E   L   L   E   K   K    38
121 ACA GGG GTT TGA                                                                  132
 39  T   G   V   *                                                                    42
```

FIG. 15

```
  1 GCCGCC ATG GCC GCG GTA GCG CTG CTC CCG GCG GTC CTG CTG GCC TTG CTG GCG CCC GAG    60
  1        M   A   A   V   A   L   L   P   A   V   L   L   A   L   L   A   P   E     18
 61 GAA TTG GGT AAA AGA GAA GTC ACA ATT CCT CCA AAA TAT AGG GAA CTA TTG GCT AAA AAG  120
 19  E   L   G   K   R   E   V   T   I   P   P   K   Y   R   E   L   L   A   K   K    38
121 GAA GGG ATC TGA                                                                  132
 39  E   G   I   *                                                                    42
```

CELL-PERMEABLE PROTEIN INHIBITORS OF CALPAIN

This application is a continuation-in-part application of U.S. Ser. No. 08/964,302, filed Nov. 4, 1997 (now U.S. Pat. No. 6,015,787).

Some of the work described herein was funded by a grant from the National Cancer Institutes (Grant No. K08-1562-05). The government may therefore have certain rights in the invention.

BACKGROUND OF THE INVENTION

Calpains, a group of ubiquitous $Ca^{2+}$-activated cytosolic proteases, are believed to play some role in cytoskeletal remodeling, cellular adhesion, shape change, and motility by cleaving membrane- and actin-associated cytoskeletal proteins (see, e.g., Beckerle et al., *Cell* 51:569–577, 1987; Yao et al., *Am. J. Physiol.* 265(pt. 1):C36–46, 1993; and Shuster et al., *J. Cell Biol.* 128:837–848, 1995). Calpains have also been implicated in the pathophysiology of cerebral and myocardial ischemia, platelet activation, NF-κB activation, Alzheimer's disease, muscular dystrophy, cataract progression, and rheumatoid arthritis.

Calpastatin is a physiological inhibitor of μ-calpain and m-calpain, which are so named because they require micromolar or millimolar concentrations of $Ca^{2+}$ ions, respectively, to achieve half-maximal activity in vitro. Calpastatin has four internally repeated domains, each of which independently binds a calpain molecule in its active, $Ca^{2+}$-bound conformation with high affinity (Mellgren et al., *The Regulation of Calpains by Interaction with Calpastatins*, and Maki et al., *Structure-Function Relationship of Calpastatins*, both in *Intracellular Calcium-Dependent Proteolysis*, Mellgren and Murachi, Eds, CRC Press, Boca Raton, Fla., 1990; and Yang et al., *J. Biol. Chem.* 269:18977–18984, 1994).

There is considerable interest in inhibitors of calpain (Wang et al., *Trends in Pharm. Sci.* 15:412–419, 1994; Mehdi, *Trends in Biochem. Sci.* 16:150–153, 1991).

SUMMARY OF THE INVENTION

The invention features methods of inhibiting a calpain (e.g., μ-calpain and/or m-calpain) in a cell (e.g., a eukaryotic cell). The method can be carried out, for example, by contacting the cell with an effective amount of a fusion protein having a first portion and a second portion, the first portion including a signal sequence capable of delivering the fusion protein into the cell and the second portion including a calpastatin peptide or a biologically active variant thereof. A calpastatin peptide (or biologically active variant thereof) will inhibit calpain activity in a standard assay for calpain activity, such as those described herein. Preferably, a calpastatin peptide (or biologically active variant thereof) will inhibit calpain activity by at least 40%, more preferably by at least 60%, and most preferably by at least 80% (e.g., 85%, 90%, 95% or more).

Calpastatin peptides include those described in Table 1. Biologically active variants of these peptides are likely to be those in which conserved amino acid residues (as shown in Table 1; e.g., see the underlined residues in SEQ ID NO:4) are either retained or replaced with an amino acid residue of the same type (i.e., peptides having one or more conservative amino acid substitutions). A conservative amino acid substitution occurs when one amino acid residue is replaced with another that has a similar side chain. Amino acid residues having similar side chains are known in the art and include families with basic side chains (e.g., lysine (Lys/K), arginine (Arg/R), histidine (His/H)), acidic side chains (e.g., aspartic acid (Asp/D), glutamic acid (Glu/E)), uncharged polar side chains (e.g., glycine (Gly/G), asparagine (Asn/N), glutamine (Gln/Q), serine (Ser/S), threonine (Thr/T), tyrosine (Tyr/Y), cysteine (Cys/C)), nonpolar side chains (e.g., alanine (Ala/A), valine (Val/V), leucine (Leu/L), isoleucine (Ile/I), proline (Pro/P), phenylalanine (Phe/F), methionine (Met/M), tryptophan (Trp/W)), beta-branched side chains (e.g., threonine (Thr/T), valine (Val/V), isoleucine (Ile/I)) and aromatic side chains (e.g., tyrosine (Tyr/Y), phenylalanine (Phe/F), tryptophan (Trp/W), histidine (His/H)).

Preferably, the calpastatin peptide includes the sequence Xaa-Xaa-Leu-Gly-Xaa-Xaa-Xaa-Xaa-Thr-Ile-Pro-Pro-Xaa-Tyr-Xaa-Xaa-Leu-Leu-Xaa-Xaa-Xaa-Xaa-Xaa-Xaa (SEQ ID NO:4), wherein Xaa at position 1 is Glu, Asp, or Lys;

Xaa at position 2 is Lys, Glu, Ala, or Asn;

Xaa at position 5 is Glu, Lys, or Ile;

Xaa at position 6 is Arg, Lys, or Asp;

Xaa at position 7 is Asp, or Glu;

Xaa at position 8 is Asp, Val, Ser, Gly, or Glu;

Xaa at position 13 is Glu, Lys, or Asp;

Xaa at position 15 is Arg, Lys, or Gln;

Xaa at position 16 is Glu, His, Lys, or Leu; and

Xaa at position 19 is Glu, Asp, Asn, Ala, or Val;

Xaa at position 20 is Lys, Asp, Gln, Asn, Thr, or Met;

Xaa at position 21 is Lys, Asp, Glu, Gly, or Asn;

Xaa at position 22 is Thr, Glu, Gly, or Lys;

Xaa at position 23 is Gly, Ala, Glu, Gln, Lys or Asp; and

Xaa at position 24 is Val, Ile, Asp or Gly.

In various preferred embodiments, the amino-terminal end of the second portion is covalently bonded to the carboxy-terminal end of the first portion by a peptide bond; the second portion has the sequence of SEQ ID NO:4; the first portion has the sequence of SEQ ID NO:3; the fusion protein has the sequence of SEQ ID NO:1; the cell is a platelet; the cell is a sickle erythrocyte; the cell is an HIV-infected cell; the cell is an endothelial cell; and the cell is a proliferating cell (e.g., a tumor cell).

In other embodiments, the invention features methods of preventing platelet aggregation. These methods can be carried out, for example, by contacting a plurality of platelets with an effective amount of a fusion protein that includes a first portion and a second portion, the first portion including a signal sequence capable of delivering the fusion protein into the cell and the second portion including a calpastatin peptide or biologically active variant thereof.

In other embodiments, the invention features methods of preventing platelet degranulation. These methods can be carried out, for example, by contacting a plurality of platelets with an effective amount of a fusion protein that includes a first portion and a second portion, the first portion including a signal sequence capable of delivering the fusion protein into the cell and the second portion including a calpastatin peptide or biologically active variant thereof.

In other embodiments, the invention features methods of inhibiting or reversing erythrocyte sickling. These methods can be carried out, for example, by contacting a sickle erythrocyte (i.e., an erythrocyte that displays a sickled morphology or that is susceptible to sickling) with an effective amount of a fusion protein that includes a first portion and a second portion, the first portion including a signal sequence capable of delivering the fusion protein into the cell and the second portion including a calpastatin peptide or biologically active variant thereof.

In other embodiments, the invention features methods of inhibiting a human immunodeficiency (HIV) virus (and thereby treating a patient who has or who is at risk of contracting AIDS). These methods can be carried out, for example, by contacting an HIV-infected cell or a cell that is susceptible to HIV infection with an effective amount of a fusion protein that has a first portion and a second portion, the first portion including a signal sequence capable of delivering the fusion protein into the cell and the second portion including a calpastatin peptide or biologically active variant thereof.

In other embodiments, the invention features methods of treating an inflammatory disorder or an unwanted immune response (e.g., an immune response that culminates in rejection of transplanted tissue). These methods can be carried out, for example, by contacting one or more of a variety of cell types (e.g., B cells, macrophages, dendritic cells or other antigen presenting cells, T cells, endothelial cells, or neutrophils) with an effective amount of a fusion protein that has a first portion and a second portion, the first portion including a signal sequence capable of delivering the fusion protein into the cell and the second portion including a calpastatin peptide or biologically active variant thereof.

In other embodiments, the invention features methods of inhibiting unwanted cellular proliferation or migration (as occurs, for example, in the event of restenosis following balloon angioplasty and in malignant cells). The method can be carried out, for example, by contacting the cell (e.g., a vascular endothelial cell or a tumor cell) with an effective amount of a fusion protein that has a first portion and a second portion, the first portion including a signal sequence capable of delivering the fusion protein into the cell and the second portion including a calpastatin peptide or biologically active variant thereof.

In other embodiments, the invention features methods for lengthening the time that platelet-containing products (e.g., blood products) can be safely stored and improving the ease with which they can be used. For example, the methods can be used to prevent platelet activation and spreading on surfaces such as tubing, heart valves, and vascular prostheses. These methods can be carried out, for example, by contacting the platelets to be stored or used with an effective amount of a fusion protein that has a first portion and a second portion, the first portion including a signal sequence capable of delivering the fusion protein into the cell and the second portion including a calpastatin peptide or biologically active variant thereof.

In various preferred embodiments of the methods described above, the amino-terminal end of the second portion is covalently bonded to the carboxy-terminal end of the first portion by a peptide bond; the second portion has the sequence of SEQ ID NO:4; the first portion has the sequence of SEQ ID NO:3; and the fusion protein has the sequence of SEQ ID NO:1.

Another aspect of the invention is a fusion protein that has a first portion and a second portion, the first portion including a signal sequence capable of delivering the fusion protein into a eukaryotic cell and the second portion including a calpastatin peptide or biologically active variant thereof. Fusion proteins of the invention encompass the biologically active variants of calpastatin described above (e.g., peptides in which conserved amino acid residues are either retained or replaced with an amino acid residue of the same type) as well as peptides having the sequence Xaa-Leu-Gly-Xaa-Xaa-Xaa-Xaa-Thr-Ile-Pro-Pro-Xaa-Tyr-Xaa-Xaa-Leu-Leu-Xaa-Xaa-Xaa-Xaa-Xaa-Xaa (SEQ ID NO:4), wherein Xaa at position 1 is Glu, Asp, or Lys;

Xaa at position 2 is Lys, Glu, Ala, or Asn;

Xaa at position 5 is Glu, Lys, or Ile;

Xaa at position 6 is Arg, Lys, or Asp;

Xaa at position 7 is Asp, or Glu;

Xaa at position 8 is Asp, Val, Ser, Gly, or Glu;

Xaa at position 13 is Glu, Lys, or Asp;

Xaa at position 15 is Arg, Lys, or Gln;

Xaa at position 16 is Glu, His, Lys, or Leu;

Xaa at position 19 is Glu, Asp, Asn, Ala, or Val;

Xaa at position 20 is Lys, Asp, Gln, Asn, Thr, or Met;

Xaa at position 21 is Lys, Asp, Glu, Gly, or Asn;

Xaa at position 22 is Thr, Glu, Gly, or Lys;

Xaa at position 23 is Gly, Ala, Glu, Gln, Lys or Asp; and

Xaa at position 24 is Val, Ile, Asp or Gly.

In still other preferred embodiments, the amino-terminal end of the second portion is covalently bonded to the carboxy-terminal end of the first portion by a peptide bond; the first portion has the sequence of SEQ ID NO:3; and the fusion protein has the sequence of SEQ ID NO:1.

Suitable calpastatin peptides include those that correspond to repeat 1 and repeat 4 of human, bovine, porcine, rabbit, or rat calpastatins (see Table 1) and can also include combinations of various repeats (e.g., the first 12 amino acids of human repeat 1 can be combined with the last 12 amino acids of rabbit repeat 4). A preferred calpastatin peptide, TIPPEY (Croall et al., *Biochem.* 33:13223–13230, 1994), is also shown in Table 1, together with some of the substitutions that could be made for amino acids in TIPPEY. A humanized amino acid sequence is shown in FIG. 16. A "calpastatin repeat" is a portion of calpastatin that binds calpain directly. Repeats 1 and 4 have the highest affinity for calpain (Kawasaki et al., *J. Biochem.* 90:1787–1793, 1989).

Moreover, additional amino acid residues may be present in the fusion protein without disrupting function. Such optional additional amino residues may be artifacts of the plasmid construction process and may be left in place as a matter of convenience. The additional residues may also constitute an epitope tag, which can be used to facilitate identification and purification of the fusion protein.

Suitable signal sequences include the 16 amino acid signal sequence of Kaposi's fibroblast growth factor (AAVALLPAVLLALLAP (SEQ ID NO:3); Rojas et al., *J. Biol. Chem.* 271:27456–27461, 1996) or variants thereof that facilitate entry of a fused heterologous peptide into a eukaryotic cell.

The cell-penetrating, calpain-inhibiting fusion peptides described herein (including those that contain fragments or other biologically active variants of calpastatin, as well as calpastatin hybrids) may be referred to below as calpastat-like fusion peptides.

The signal sequence can also be the 16 amino acid signal sequence of antennapedia (RQIKIWFQNRRMKWKK (SEQ ID NO:6); Prochiantz, *Curr. Opinion in Neurobiol.* 6:629, 1996) or variants thereof that facilitate entry of a fused heterologous peptide into a eukaryotic cell.

TABLE 1

Calpastatin peptides

Repeat 1

| | | |
|---|---|---|
| human | EELGKREVTTPPKYRELLEKKEGI | (SEQ ID NO:8) |
| bovine | EELGKRESTPPPKYKELLNKEEGI | (SEQ ID NO:9) |
| pig | EELGKREVTLPPKYRELLDKKEGI | (SEQ ID NO:10) |
| rabbit | EELGKREVTIPPKYRELLEKKTGV | (SEQ ID NO:11) |
| rat | EALGIKEGTIPPEYRKLLEKNEAI | (SEQ ID NO:12) |

Repeat 4

```
human        DKLGERDDTIPPEYRHLLDDNGQD  (SEQ ID NO:13)
bovine       DKLGERDDTIPPKYQHLLDDNKEG  (SEQ ID NO:14)
pig          DKLGERDDTIPPEYRHLLDKDEEG  (SEQ ID NO:15)
rabbit       DKLGERDDTIPPEYRHLLDQGEQD  (SEQ ID NO:16)
rat          EKLGERDDTIPPEYRHLLDNDGKD  (SEQ ID NO:17)
TIPPEY:      EKLGERDDTIPPEYRELLEKKTGV  (SEQ ID NO:4)
Substitu-    DE  KKEV   K KH   DDDEAI
tions:        A I  S       QK  NQEGED
                    G           NGKQG
                                  N K
             KN   D E    D L  AT  D
                                 VM
```

The methods and compositions described herein have numerous advantages. For example, the fusion proteins include a signal sequence that allows the protein to enter a cell and, therein, inhibit calpains. Moreover, this inhibition is expected to be reversible (since the interaction of calpastatin with calpain is reversible; see, e.g., Anagli et al., *European J. Biochem.* 241:948–954, 1996).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, exemplary methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Various features and advantages of the invention will be apparent from the following detailed description, and from the claims.

BRIEF DESCRIPTION OF THE DRAWINGS

FIGS. 7A–7D are graphs showing the production of HIV p24 antigen (indicated by "mean fold activity") in U1 cells treated with various concentrations of calpastat. The mean fold activity was recorded at 24(A), 48(B), 72(C), or 96(D) hours following thapsigargin induction. FIG. 7E) and thapsigargin-induced HIV-1 replication (FIG. 7F).

FIG. 15 depicts a DNA sequence for calpastat (SEQ ID NO:20) and the amino acid sequence it encodes (SEQ ID NO:21).

FIG. 16 depicts a DNA sequence for a calpain inhibitor related to calpastat (SEQ ID NO:22) and the amino acid sequence it encodes (SEQ ID NO:23).

DETAILED DESCRIPTION OF THE INVENTION

Figure 1:
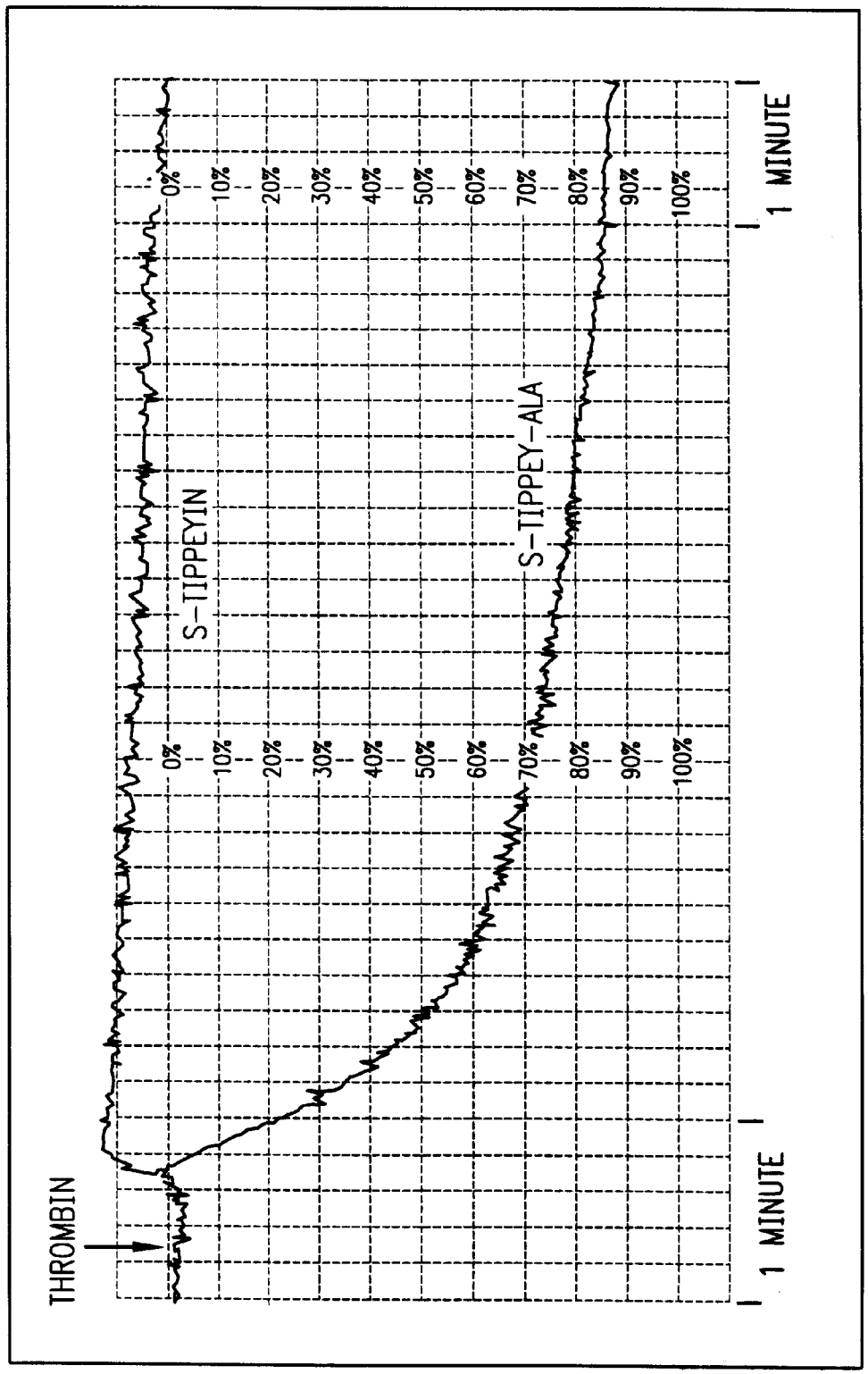
FIG. 1 is a graph showing thrombin-induced platelet aggregation in the presence of 50 μM S-TIPPEYIN (also known as calpastat; upper line) or S-TIPPEY-ala (also known as calpastat-ala; lower line).

Soluble fusion proteins that can penetrate cells and inhibit calpain are described herein for the first time. These proteins include a cell-penetrating sequence (e.g., the signal sequence of Kaposi's fibroblast growth factor (kFGF)) and a calpain-inhibiting sequence (e.g., calpastatin or a biologically active derivative thereof).

The sequence of one such fusion protein, calpastat (also known as S-TIPPEYIN), is provided below (SEQ ID NO:1). The first 16 amino acids of calpastat correspond to the kFGF signal sequence, and the next 24 amino acids correspond to (i.e., are identical to) a biologically active derivative of calpastatin. This fusion protein loses activity when seven particular amino acid residues are replaced with alanine (as in the peptide S-TIPPEY-ala (SEQ ID NO:2)). Most of the seven amino acids replaced (those underlined in the sequence of S-TIPPY-ala, below) are highly conserved in calpastatin.

S-TIPPEYIN (i.e., calpastat):
NH$_2$ -AAVALLPAVLLALLAPEKLGERDDTIPPEYREL
LEKKTGV-COOH (SEQ ID NO:1)
S-TIPPEY-ala (i.e., calpastat-ala):
NH$_2$-AAVALLPAVLLALLAPEKLAERADAAAPE
AAELLEKKTGV-COOH (SEQ ID NO:2)

Other calpastat-like fusion proteins can contain a biologically active peptide fragment of calpastatin or a biologically active variant of that fragment. Moreover, the fusion peptides of the invention (regardless of whether they contain full length calpastatin peptides or fragments or biologically active variants thereof) can contain the consensus amino acid residues found in repeat 1 and repeat 4 of mammalian (e.g., human, bovine, porcine, rabbit, or rat) calpastatins (i.e., they can be hybrid peptides). Functional variants of calpastatin peptides (i.e., biologically active variants), including hybrid peptides, are within the scope of the invention even when they do not contain all of the amino acid residues present in the consensus sequence.

The ability of calpastatin peptides (including hybrid peptides) to inhibit calpain can be assessed in cell extracts or intact cells as described in the examples below or in other assays known in the art (e.g., in the assay disclosed by Bronk et al., *Am. J. Physiol.* 264:G744–751, 1993 or modified versions thereof). For instance, calpain activity can be monitored in intact cells by measuring Ca$^{2+}$ ionophore-specific peptidyl hydrolysis of the peptidyl-7-amino bond of a calpain substrate (e.g., succinyl-leucyl-leucyl-valyn-tyrosyl-7-amino-4-methylcoumarin (suc-LLVY-AMC; SEQ ID NO:7)). To assay calpain activity in this way, cells are washed and re-suspended in HEPES-buffered (10 mM HEPES-NaOH, pH 7.4) Hank's balanced salts solution (without Ca$^{2+}$) at about 2.5×10$^5$ cells/ml and placed on ice. To assay calpain activity, the cell suspension is pre-warmed to 37° C. for 10 minutes with stirring in an SLM ALMINCO 8000 fluorimeter. At t=−1 minute, ionomycin in DMSO (at a final concentration of 2.5 $\mu$M) or DMSO alone (negative control) is added to the cells. At t=0 minute, suc-LLVY-AMC (SEQ ID NO:7) is added to a final concentration of 50 $\mu$M. The initial rate of substrate cleavage, which is linear, is measured by spectroscopy at 2 to 3 minutes. The excitation wavelength is 360±2 nm and the emission detection wavelength is 460±10 nM. The ionomycin-dependent rate of substrate cleavage is subtracted from the ionomycin-independent rate of substrate cleavage to obtain the Ca$^{2+}$-dependent rate. AMC standard solutions are used to determine moles of AMC generated from emission data. Cell viability can be monitored during the assay by trypan blue exclusion.

Calpastat-like fusion proteins can be produced by cultured cells (e.g., *E. coli,* yeast, insect cells, or mammalian cells) transfected with nucleic acid molecules that encode the fusion protein and have appropriate expression control sequences (see, e.g., U.S. Pat. No. 5,648,244). The nucleic acid molecules can be introduced into the cultured cells by standard transfection techniques, and the recombinantly produced peptides can then be extracted and purified by techniques well known in the art (e.g., immunoaffinity purification). For an exemplary cloning procedure, see Example 15, below. It is well within the ability of one of ordinary skill in the art to carry out the cloning procedure described in Example 15 or any comparable cloning procedure known in the art.

Calpastat-like fusion peptides can also be produced in significant amounts (i.e., in amounts sufficient for commercial or experimental use) by chemical synthesis. For example, calpastat-like peptides can be synthesized using solid phase N-(9-fluorenyl) methoxycarbonyl/N-methylpyrrolidone (Fmoc) chemistry (Jacobs et al., *J. Biol. Chem.* 269:25494–25501, 1994). Calpastat, calpastat-ala, and the 24 amino acid calpastatin peptide produced by chemical synthesis were found to be greater than 95% pure by HPLC and to have the correct molecular mass and protein sequence when assayed by mass spectrometry and Edman degradation. Peptide concentrations can be determined by quantitative amino acid analysis.

Calpastat-like fusion proteins have numerous uses. They can be used, for example, to reduce coronary thrombosis in coronary bypass surgery, to reduce vascular thrombosis and restenosis in angioplasty, to reduce the progression of an infarct in the event of myocardial infarction or stroke (including treatment in the acute setting), and to treat subarachnoid hemorrhage or vasospasm, muscular dystrophy, cataracts, sickle cell crisis, HIV infection, Alzheimer's Disease, brain aging, traumatic brain injury, joint inflammation, and arthritis.

Calpastat-like fusion proteins can be administered to a patient who exhibits symptoms of one or more of the illnesses or conditions listed above, as well as to patients who have not yet exhibited symptoms (i.e., the fusion proteins can be administered prophylactically). For instance, a hybrid fusion protein can be administered to a patient who has undergone angioplasty and shows signs of restenosis. Alternatively, the protein can be administered before angioplasty to prevent the occurrence of restenosis.

The fusion proteins can be used alone or in combination and can be administered with a pharmaceutically acceptable carrier (e.g., physiological saline). The carrier can be selected on the basis of the mode and route of administration, according to standard pharmaceutical practice. Suitable pharmaceutical carriers, as well as useful pharmaceutical necessities, are described in *Remington's Pharmaceutical Sciences* (E. W. Martin), a standard reference text in this field, and in the USP/NF.

The therapeutic compositions described above can also include agents that augment or potentiate the therapeutic activity of the fusion proteins. For example, the compositions can include agents that increase the biological stability of the fusion proteins or that increase the ability of the fusion protein to selectively penetrate a target cell. For example, to enhance targeting, fusion peptides can be encapsulated in liposomes coated with ligands that bind cell-surface receptors expressed primarily or exclusively on the target cells. Other agents can be selected depending on various considerations, such as the disease or disorder to be treated and the potential for adverse interactions with other drugs prescribed for the patient.

Therapeutic compositions containing fusion proteins can be administered in dosages determined to be appropriate by one skilled in the art. It is expected that the dosages will vary, depending upon the pharmacokinetic and pharmacodynamic characteristics of the particular agent and its mode and route of administration; the age, weight, and general health of the recipient (renal and hepatic function are important considerations); the nature and extent of the disease or disorder; the frequency and duration of the treatment; the type of concurrent therapy (if any); and the desired effect. It is expected that a useful dosage will contain between about 0.1 to 300 mg of active ingredient per kilogram of body weight. Ordinarily, 1 to 100 mg, and preferably 10 to 50 mg of active ingredient (nucleic acid or protein) per kilogram of body weight per day, given in divided doses or in sustained release form, is appropriate.

The therapeutic compositions of the invention may be administered to a patient by any appropriate mode. For example, they may be administered orally or parenterally (e.g., intraperitoneally or intravenously). Alternatively, it may be desirable to administer the compositions during a surgical procedure. For example, a composition can be applied to the target tissue during angioplasty. The treatments of the invention may be repeated as needed, as determined by one skilled in the art.

The therapeutic or prophylactic efficacy of fusion proteins can be assessed using animal models of the diseases or conditions described above. Animal models are well known to those of ordinary skill in the art (see also the examples below).

Administration of DNA sequences encoding calpastat-like fusion proteins is also within the scope of the invention and is described below (see, e.g., Example 17).

Calpastat-like fusion proteins can also be used in vitro. For instance, fusion proteins can prevent platelet aggregation and degranulation and can, therefore, be used to preserve platelets stored in blood banks (e.g., platelets preserved at temperatures that inhibit the growth of microorganisms, generally 4° C.–15° C.). To improve platelet storage, an appropriate amount of a fusion protein (e.g., calpastat at about 1–100 µM) can be added to platelet preparations.

Calpastat-like fusion proteins can also be used to facilitate autologous blood transfusions in sickle cell patients and patients with sickle trait by preventing irreversible sickling during blood storage. Thus, fusion proteins can be used to promote storage and use of blood from sickle cell patients or patients with sickle trait (Asakura et al., *Blood Cells, Molecules & Diseases* 22:297–306, 1996; Vichinsky et al., *New Engl. J. Med.* 322:1617–1621, 1990).

Described below are examples which demonstrate that calpastat, which is pharmacologically active at concentrations ranging from about 5 nM to about 100 µM: (1) prevents platelet aggregation and degranulation; (2) inhibits erythrocyte sickling; and (3) inhibits $Ca^{2+}$-mediated activation of HIV-1 provirus. While the studies described in these specific examples use calpastat, other fusion proteins of the invention could be used in a similar manner. The examples also include protocols that can be used to optimize the therapeutic effectiveness of the new fusion proteins in animal models.

Unless otherwise noted, the materials used in the studies described below were obtained from commercial suppliers. Sepharose 2B was obtained from Pharmacia Biotech (Upsala, Sweden); pure µ-calpain (porcine erythrocyte) was obtained from Chemicon; succinyl-LLVY-AMC (SEQ ID NO:7) was obtained from Bachem; A23187 was obtained from LC Labs; human alpha-thrombin was obtained from Hematologic Technologies (Essex Junction, Vt.); anti-P-selectin antibodies conjugated to phycoerythrin were obtained from Becton Dickinson (San Jose, Calif.); Oregon Green-phalloidin was obtained from Molecular Probes (Eugene, Oreg.). All other chemicals were ACS grade or better and were obtained from Sigma Chemical Company (St. Louis, Mo.).

The following examples are meant to illustrate the methods and materials of the present invention. Suitable modifications and adaptations of the conditions and parameters described below will be obvious to those of ordinary skill in the art and are within the spirit and scope of the present invention.

EXAMPLE 1
Inhibition of Platelet Aggregation

The experiments described below demonstrate that calpastat, but not the calpastat mutant, S-TIPPEY-ala, effectively inhibits platelet aggregation.

In one series of experiments, platelets were purified from serum on a SEPHAROSE 2B column in PIPES buffered saline containing glucose, pre-incubated with 45 µM calpastat or S-TIPPEY-ala for 30 minutes at 37° C., and placed in a cuvette in a BIODATA aggregometer. The aggregometer measures turbidity of the solution by nephlometry (light scatter). Aggregation was induced with thrombin (0.1 to 1 unit/ml) or the thrombin receptor agonist peptide SFLLR (SEQ ID NO:5). Calpastat inhibited platelet aggregation, with maximal inhibition achieved at 45 µM calpastat. In contrast, S-TIPPEY-ala had no activity. A version of S-TIPPEYIN lacking the signal sequence similarly had no activity.

This result demonstrates that calpastat can effectively inhibit platelet aggregation and that the seven conserved amino acids mutated in S-TIPPEY-ala are essential for calpastatin function. This result also demonstrates that the platelet inhibitory activity of calpastat lies in the calpastatin portion of calpastat, not the amino-terminal kFGF signal sequence which makes it cell-penetrating.

In another series of experiments, gel filtered platelets were obtained and tested as follows. Blood from healthy, aspirin-free volunteers was collected by venipuncture into 4% sodium citrate (9:1 v/v, final concentration 0.4%) and centrifuged at 200×g for 20 minutes to obtain platelet rich plasma (PRP). Following incubation with apyrase (4 units/ml for 5 minutes at room temperature), platelets were purified from PRP by gel-filtration at room temperature using a Sepharose 2B column equilibrated in PIPES buffer (25 mM PIPES pH 6.8, 140 mM NaCl, 4 mM KCl, and 0.1% glucose) (Hsu-Lin, et al., *J. Biol. Chem.* 259:9121–9126, 1984). Final gel filtered platelet concentrations were about $1.5 \times 10^8$ cells/ml.

Gel filtered platelets (250 µl aliquots at $1.6 \times 10^8$ 1/ml) were incubated with the indicated concentration of calpastat or mutant calpastat-ala for either 20 or 30 minutes at 37° C. in the absence of calcium and stirring. To test peptidyl calpain inhibitors, platelets were preincubated with the indicated concentration of calpeptin, MDL, E64d, DMSO (vehicle control) or $NH_4Cl$ (cathepsin control) for 10 minutes at 37° C. Following incubation, platelets were recalcified ($CaCl_2$, 2 mM) and stimulated with 0.05–1.0 unit/ml thrombin, while being stirred (1400 rpm) at 37° C. The sensitivity of platelet preparations to thrombin decreased over the course of a given experiment. The thrombin concentration used was to elicit robust aggregation and varied between 0.05 and 1.0 U/ml. Aggregation was measured using a Bio-Data lumi-aggregometer. Percent inhibition of aggregation was measured at 4 minutes following the onset of aggregation. The initial rate of aggregation during the first 15 seconds for treated vs. untreated samples was used to calculate the $IC_{50}$ for each inhibitor.

Calpastat effectively inhibited the extent of platelet aggregation by 60 to 95% at four minutes following the onset of aggregation (FIG. 1). In contrast, calpastat-ala (FIG. 1) or the calpastatin 24-mer had no measurable effect on platelet aggregation (Table 2; NI=no inhibition). By comparing the initial rate of thrombin-induced aggregation at various concentrations of inhibitor, the $IC_{50}$ of calpastat was determined to be 50 (Table 2).

Three immediately acting peptidyl calpain inhibitors (calpeptin, MDL and E64d) also inhibited thrombin-induced platelet aggregation. Following a 10 minute pre-incubation period, calpeptin, MDL, and E64d inhibited the initial rate of platelet aggregation with $IC_{50}$'s of 150, 240, and 340 μM, respectively (Table 2). At high micromolar concentrations, these peptidyl compounds also inhibit members of the cathepsin family of lysosomal proteases. To test whether the peptidyl calpain inhibitors prevent aggregation by inhibiting cathepsins as well as calpain, platelets were pre-incubated with 10 mM $NH_4Cl$, which maximally inhibits cathepsin function (Hopgood et al., *Biochem J.* 164:399–407, 1977). Pretreatment of platelets with 10 mM $NH_4Cl$ does not affect platelet aggregation (Table 2). Thus, inhibition of aggregation by peptidyl calpain does not occur through inhibition of cathepsins. Inhibition of aggregation by calpastat and by peptidyl calpain inhibitors together demonstrate that calpain plays a regulatory role in the intracellular events leading to platelet aggregation.

TABLE 2

| Inhibitor | $IC_{50}$ (μM) |
| --- | --- |
| Calpastat | 50 |
| Calpastatin 24mer | NI |
| Calpastat-ala | NI |
| Calpeptin | 150 |
| MDL | 240 |
| E64d | 340 |
| $NH_4Cl$ (10 mM) | NI |

EXAMPLE 2
Inhibition of α-Granule Secretion

To determine whether S-TIPPEYIN could inhibit α-granule secretion in platelets, surface expression of P-selectin, which indicates α-granule secretion, was induced with the thrombin peptide SFLLR (SEQ ID NO:5) and analyzed by flow cytometry using an antibody against P-selectin. Blood from healthy volunteers was collected into sodium citrate (4% w/v) and centrifuged at 200×g for 10 minutes to prepare platelet-rich plasma (PRP), from which platelets were subsequently purified by gel filtration using a SEPHAROSE 2B column in PIPES buffer. Twenty μl of platelets (approximately $2 \times 10^8$ platelets/ml) were aliquoted into eppendorf tubes and one μl of S-TIPPEYIN, TIPPEYIN (lacking the signal peptide sequence), or S-TIPPEY-ala was added to achieve final concentrations of 6.25, 12.5, 25, 50, or 100 μM. The platelets were then incubated for 2 hours at 37° C. and subsequently exposed to either 1 μl PBS (unstimulated) or 1 μl of SFLLR (SEQ ID NO:5; stimulated) at the indicated concentration. After 30 seconds, a 7.5 μl aliquot was transferred to an eppendorf tube containing non-immune serum having antibodies that were conjugated to phycoerythrin. Following a 20 minute incubation at room temperature, the mixture was diluted with 1 ml of 2% paraformaldehyde and incubated at 4° C. for two hours. Antibody binding to platelet surface P-selectin was quantified using a FACSCAN flow cytometer (Becton Dickerson, San Jose, Calif.). Results were reported as the geometric mean of the relative fluorescence.

Figure 2:
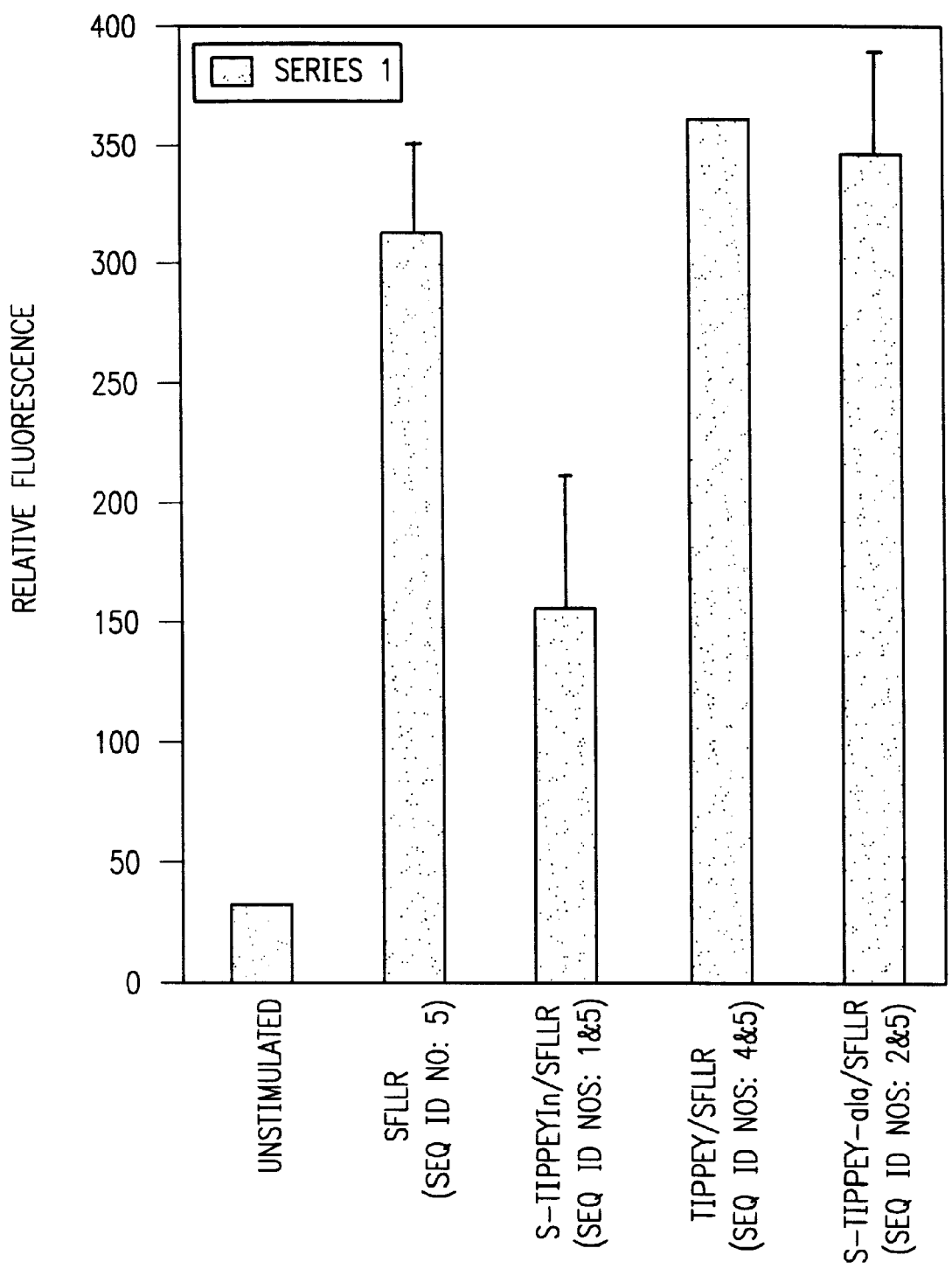
FIG. 2 is a bar graph comparing the inhibition of P-selectin surface expression by S-TIPPEYIN, TIPPEY (i.e., the calpastatin peptide portion of S-TIPPEYIN), and S-TIPPEY-ala. SFLLR indicates thrombin peptide stimulation.

As shown in FIG. 2, stimulation of gel-filtered platelets with SFLLR (50 μM) results in an approximately 10-fold increase in surface P-selectin expression (compare the bars marked respectively "unstimulated" and "SFLLR"). Pre-incubation with S-TIPPEYIN resulted in only a 5-fold increase in P-selectin surface expression (compare the bars marked respectively "unstimulated" and "S-TIPPEYIN/ SFLLR" (SEQ ID NO:5)). In contrast, pre-incubation with TIPPEY, a corresponding peptide lacking the kFGF signal sequence, had little effect on SFLLR (SEQ ID NO:5)-induced P-selectin surface expression (see the bar marked "TIPPEY/SFLLR" (SEQ ID NO:5)). Similarly, a peptide in which the seven conserved residues of calpastat were mutated to alanine had no effect on SFLLR (SEQ ID NO:5)-induced P-selectin surface expression (see the bar marked "S-TIPPEY-ala/SFLLR" (SEQ ID NO:5)).

Figure 3:
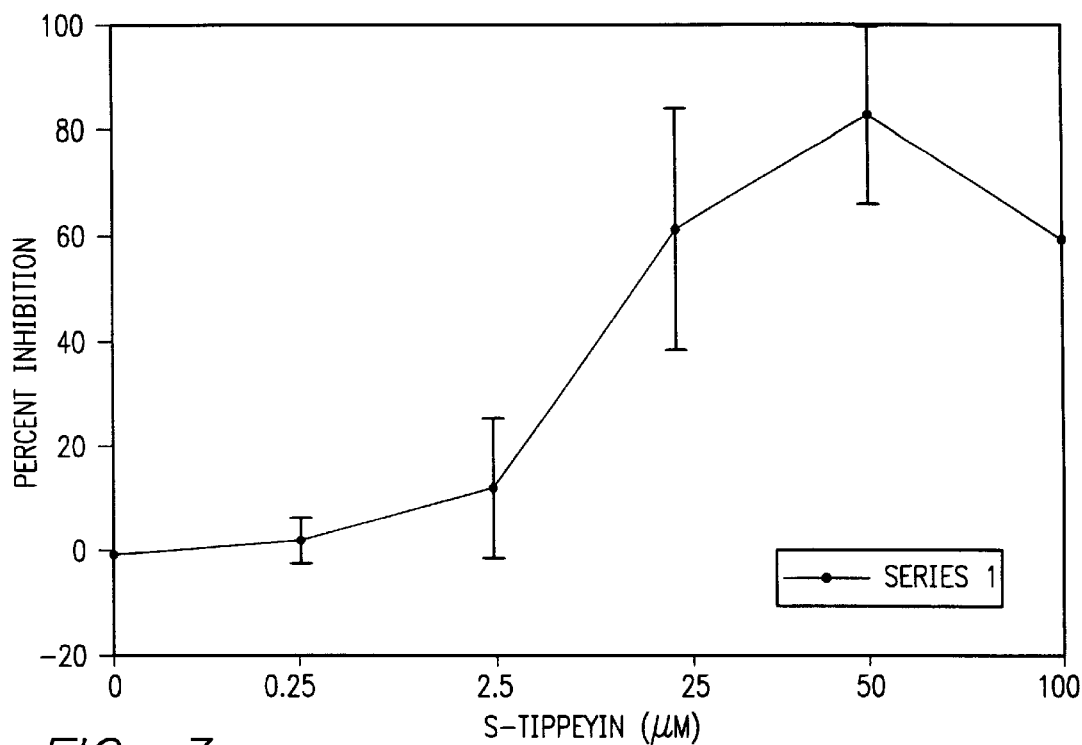
FIG. 3 is a graph showing the dose-dependent inhibition of P-selectin surface expression by S-TIPPEYIN.

The inhibitory effect of S-TIPPEYIN did not result from inhibition of the P-selectin antibody by surface P-selectin, since incubation of platelets with S-TIPPEYIN following exposure to SFLLR (SEQ ID NO:5) had no effect on the binding of antibody to surface expressed P-selectin. As shown in FIG. 3, S-TIPPEYIN inhibits the surface expression of P-selectin in a dose-dependent manner. Half-maximal inhibition occurred at about 15–20 μM, and maximal-inhibition occurred at about 40–60 μM.

S-TIPPEYIN also inhibited P-selectin surface expression induced by the ionophore A23187.

To further confirm that calpain regulates the surface expression of P-selectin, the inhibitory effects of three rapidly acting, but less specific, peptidyl calpain inhibitors (calpeptin, MDL, and E64d) were also tested. Platelets were pre-incubated with increasing concentrations of calpeptin, MDL, E64d, or DMSO (vehicle control) for ten minutes prior to stimulation with SFLLR. Calpeptin, MDL, and E64d each inhibited P-selectin surface expression with $IC_{50}$'s between 200 and 300 μM. In contrast, calpastat inhibits P-selectin expression in a dose-dependent manner with half-maximal inhibition occurring at a concentration of 30 μM. These results, together with those derived using the specific inhibitor calpastat, demonstrate a novel role for calpain in the regulation of α-granule exocytosis.

EXAMPLE 3
Inhibition of Ionophore-Dependent Calpain Degradation of Two Substrates in Platelets To investigate whether calpastat inhibits calpain activity in platelets, the ionophore-dependent proteolysis of actin binding protein (ABP; about 280 kDa) and talin (about 240 kDa), both of which are substrates of both μ- and m-calpains, was examined as follows.

Platelets were pre-incubated with $ZLLYCHN_2$, DMSO (solvent for $ZLLY-CHN_2$), calpastat, or HEPES buffer (buffer for calpastat), and then treated with or without ionophore A23187 for 5, 8, or 10 minutes. The platelets were then gel-purified as described above. Whole cell lysates were prepared and fractionated by SDS polyacrylamide gel electrophoresis. The data showed that both $ZLLY-CHN_2$ and calpastat inhibited A23187-dependent calpain degradation of ABP and talin in platelets at all three time points examined. Nonetheless, only calpastat inhibited platelet aggregation and secretion.

EXAMPLE 4
Delay of Hypoxia-Induced Sickling of Sickle Erythrocytes and Inhibition of Irreversible Sickling Calpastat was examined for its ability to inhibit sickling of red blood cells isolated from sickle cell patients. S-TIPPEY-ala, which demonstrates no inhibition of purified μ-calpain, was used as a control peptide.

To examine sickling, a wet preparation of red blood cells (as opposed to a dried smear) was made by placing blood under a coverslip on a glass slide. The slide was placed under a light microscope, and the number of cells displaying sickled morphology was counted. $Na_2S_2O_5$ was used to increase the rate of sickling.

Figure 4:
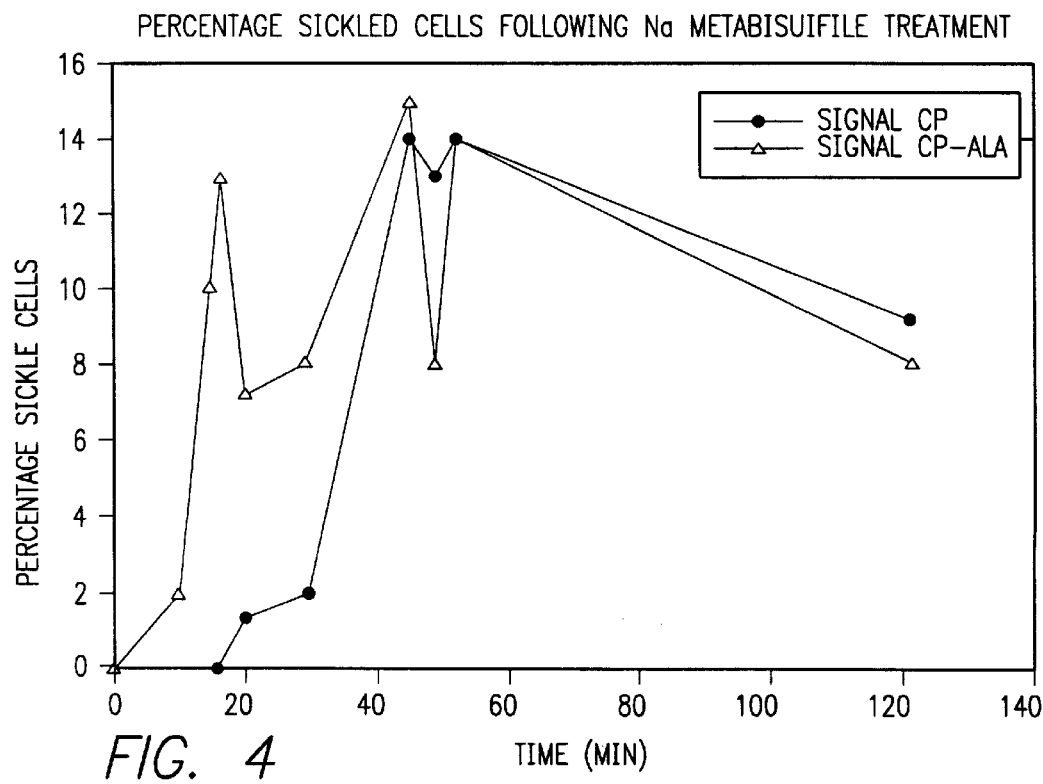
FIG. 4 is a graph showing the time course of $Na_2S_2O_5$-induced erythrocyte sickling in the presence of calpastat ("signal-CP") or S-TIPPEY-ala ("signal-CP-ala").

When EDTA-anticoagulated peripheral blood from a sickle cell patient was preincubated with calpastat for 10 minutes prior to exposure to sodium metabisulfite ($Na_2S_2O_5$), there was a significant delay (about 30 minutes) in sickling. The time course of sickling is shown in FIG. 4 for this patient. There was no detectable difference in the final percentage of sickled cells.

Figure 5:
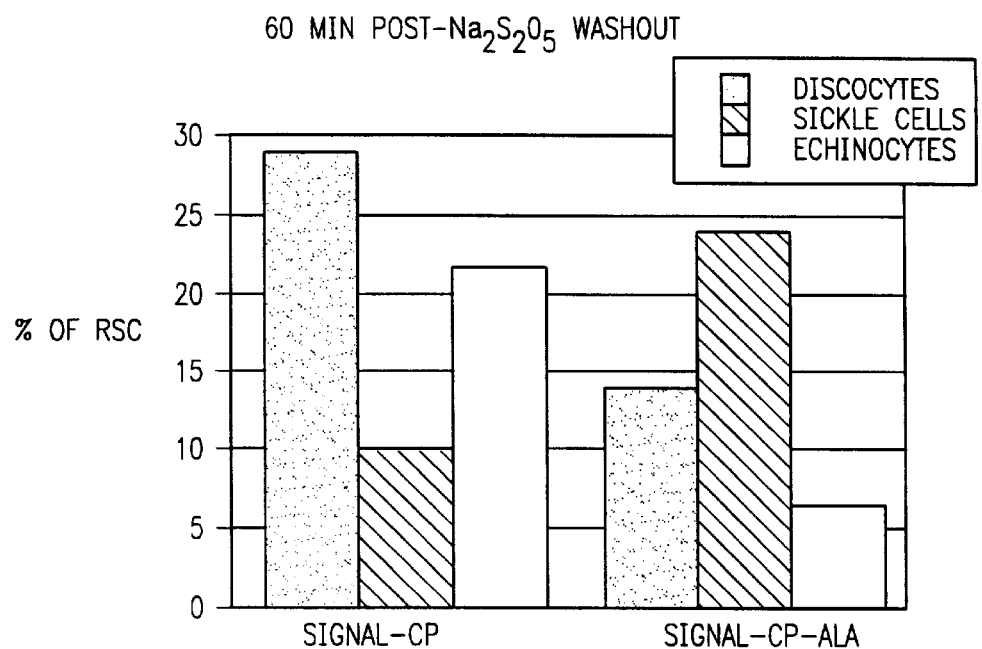
FIG. 5 is a bar graph showing the percentages of discocytes, sickle cells, and echinocytes 60 minutes after removal of $Na_2S_2O_5$. The erythrocytes (i.e., RBCs) were pre-treated with calpastat ("signal-CP") or S-TIPPEY-ala ("signal-CP-ala").

In a second experiment, the effect of calpastat on recovery from sickling was measured. Blood from the same patient was incubated with $Na_2S_2O_5$ for two hours in a microfuge tube. The supernatant plasma was then removed from the settled erythrocytes and the erythrocytes were diluted in four volumes of saline. The washed erythrocytes were then incubated in saline, and Wright-Giemsa stained smears were made 60 minutes following the washout of $Na_2S_2O_5$. The percentage of sickled cells in the microfuge tube preparation was found to be at least 2-fold greater than in the microscope slide preparation. Sixty minutes following the $Na_2S_2O_5$ washout, the percentage of discocytes was two-fold greater and the percentage of sickled cells two-fold lower in calpastat-treated cells as compared to S-TIPPEY-ala-treated cells. The percentages of discocytes, sickled cells, and echinocytes are shown in FIG. 5.

These observations suggest that calpastat delays the onset of sickling in erythrocytes and facilitates the recovery of discocytes following sickling in vitro.

EXAMPLE 5
Inhibition of HIV Provirus Activation

Thapsigargin (Tpg), an inhibitor of the $Ca^{2+}$-dependent ATPase, has been demonstrated to induce intracellular $Ca^{2+}$ leakage and activation of HIV-1 proviral transcription and virion release. Calpastat was examined for its ability to inhibit thapsigargin-induced HIV-1 activation in U1 promonocytes.

U1 is a human promonocytic cell line that is chronically infected with HIV-1 and that constitutively expresses low levels of HIV-1. U1 cells are derived from U937 cells, which are acutely infected with HIV-1, and possess two integrated copies of HIV-1 pro-viral DNA. In the present experiment, $1\times10^6$ cells/ml were treated with various dosages of calpastat and incubated for one hour at 37° C. After incubation, various concentrations of Tpg were added to the calpastat-treated cells and aliquoted into a 24-well plate. To observe the stimulation of HIV-1 activity by Tpg, equivalent numbers of cells were treated with Tpg alone. The cells were then incubated at 37° C. for up to four days, and supernatants from the cell culture were collected each day to measure HIV-1 activity. The viability of cells treated with both Tpg and calpastat were determined each day by Trypan-blue exclusion test. The HIV-1 activity in the collected supernatants was determined by measuring the HIV-1 p24 core antigen protein by ELISA (Dupont Medical Products, Boston, Mass.) according to the manufacturer's instructions.

Figure 6:
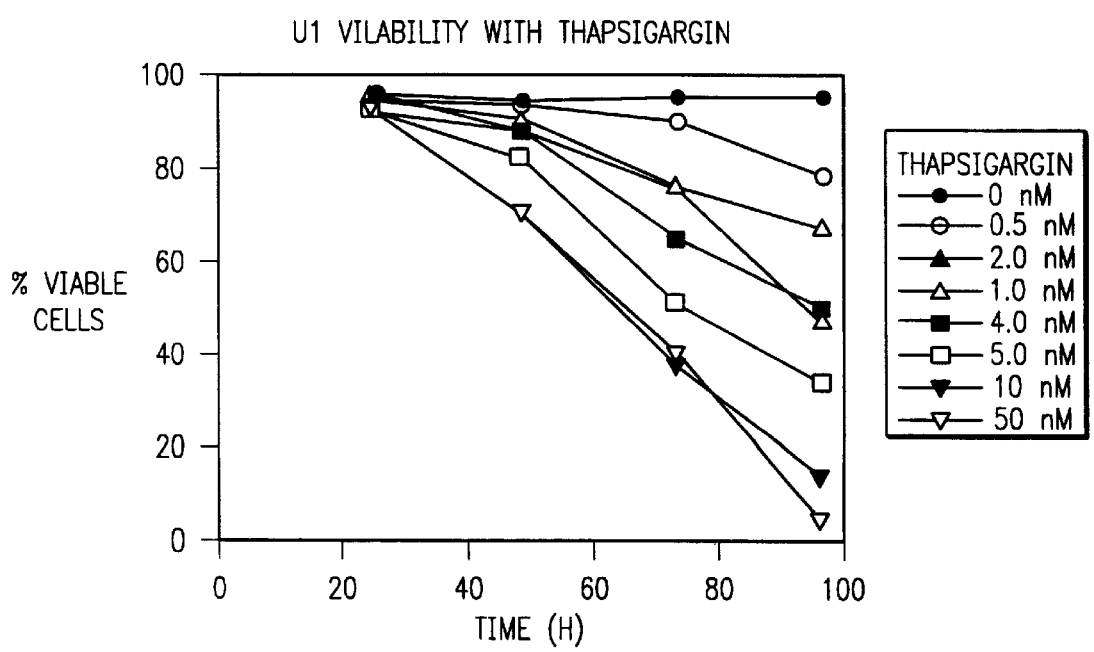
FIG. 6 is a graph showing the time course of the viability of U1 cells treated with the indicated concentrations of thapsigargin.

The data showed that Tpg-induced activation of HIV-1 occurred over a narrow concentration range, with minimal induction at 1 nM (1.37-fold induction of virus at 24 h) and maximal induction at 5 nM (20-fold induction at 24 h). Increasing doses of Tpg correlated with decreasing cell viability after 24 hours of incubation (FIG. 6). For instance, U1 cell viabilities at 96 hr were about 50% and 5% in the presence of 4.0 and 50 nM Tpg, respectively.

Five µM calpastat decreased mean fold viral production by 47, 44, 55 and 61% at 24, 46, 72 and 96 hours of Tpg stimulation, respectively (FIGS. 7A–7D). These results were highly statistically significant and indicated that calpastat inhibits HIV-1 release from infected cells by about 50%.

Figure 7E:
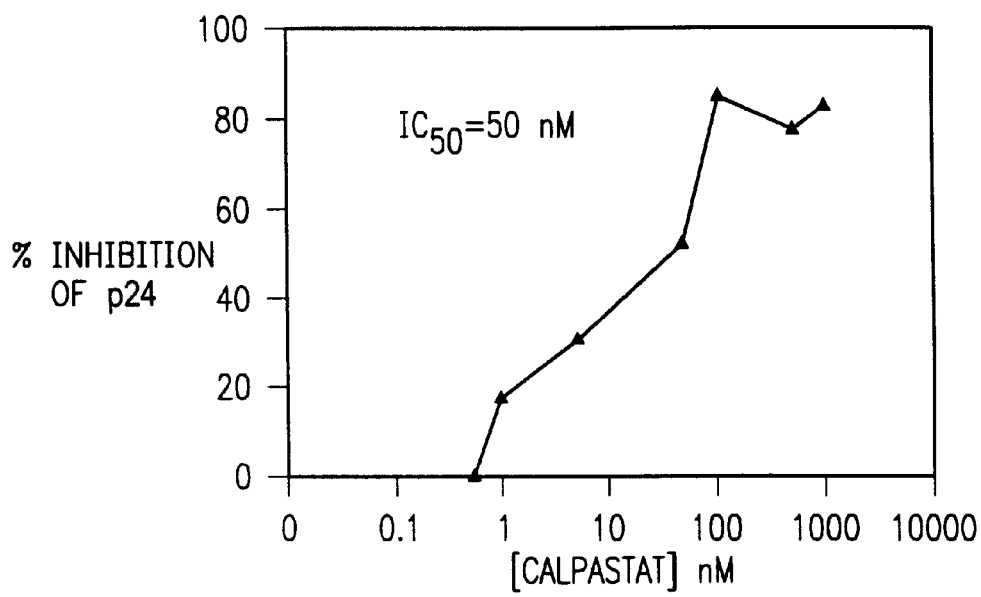
FIGS. 7E and 7F are graphs showing that Calpastat inhibits HIV-1 replication ($IC_{50}$=50 nM.
Figure 7F:
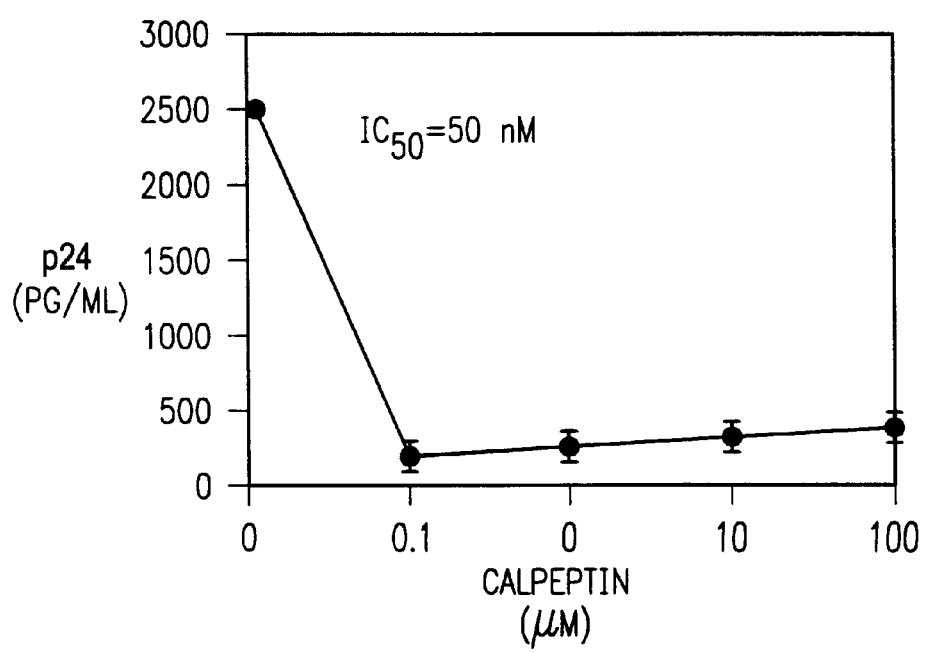

In another series of experiments, U1 cells, which are latently infected with HIV-1 provirus, were plated at $10^6$ cells/well in 1 ml of medium and treated with varying concentrations of either calpastat (FIG. 7E) or calpeptin (benzyloxycarbonyl-leucyl-norleucinal) (FIG. 7F) for 45 minutes before addition of thapsigargin (4 nM final concentration). The viability of U1 monocytes was 90% at 48 hours of thapsigargin (4 nM) treatment, in the presence or absence of calpain inhibitors. After 48 hours of stimulation, HIV-1 p24 antigen levels were determined in 200 µl of tissue culture supernatant, using a p24 ELISA (DuPont). All assays were performed on triplicate cultures. Mean values and standard deviations are shown for each concentration of inhibitor (FIGS. 7E–7F).

Figure 8:
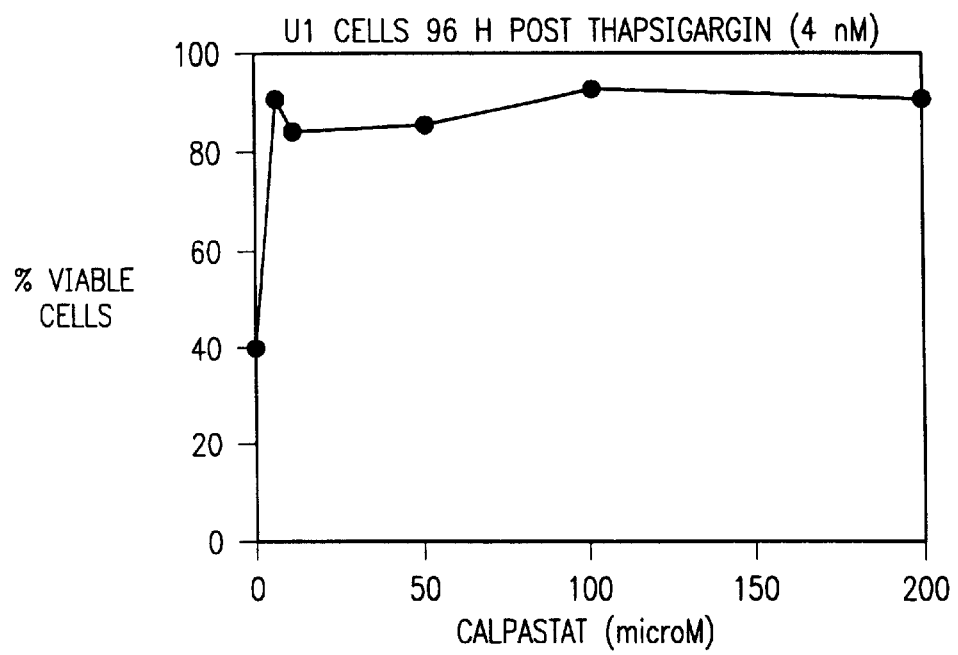
FIG. 8 is a graph showing the percentage of viable cells treated with various concentrations of calpastat at 96 hours following thapsigargin induction.

U1 viability studies confirmed that inhibition of HIV-1 activation correlates with increase in cell viability. Calpastat, at a concentration of 5 µM, was shown to increase the viability of U1 cells in 4 nM Tpg from 40% to 90% at 96 hr (FIG. 8). This result demonstrates that calpastat prevents cell death caused by HIV-1 activation.

EXAMPLE 6
Inhibition of Calpain Activity

To assess the ability of calpastat to inhibit calpain activity, a fluorometric calpain assay was performed. The assay determined specific peptidyl hydrolysis of the peptidyl 7-amino bond of suc-LLVY-AMC (SEQ ID NO:7) by calpain.

Figure 9:
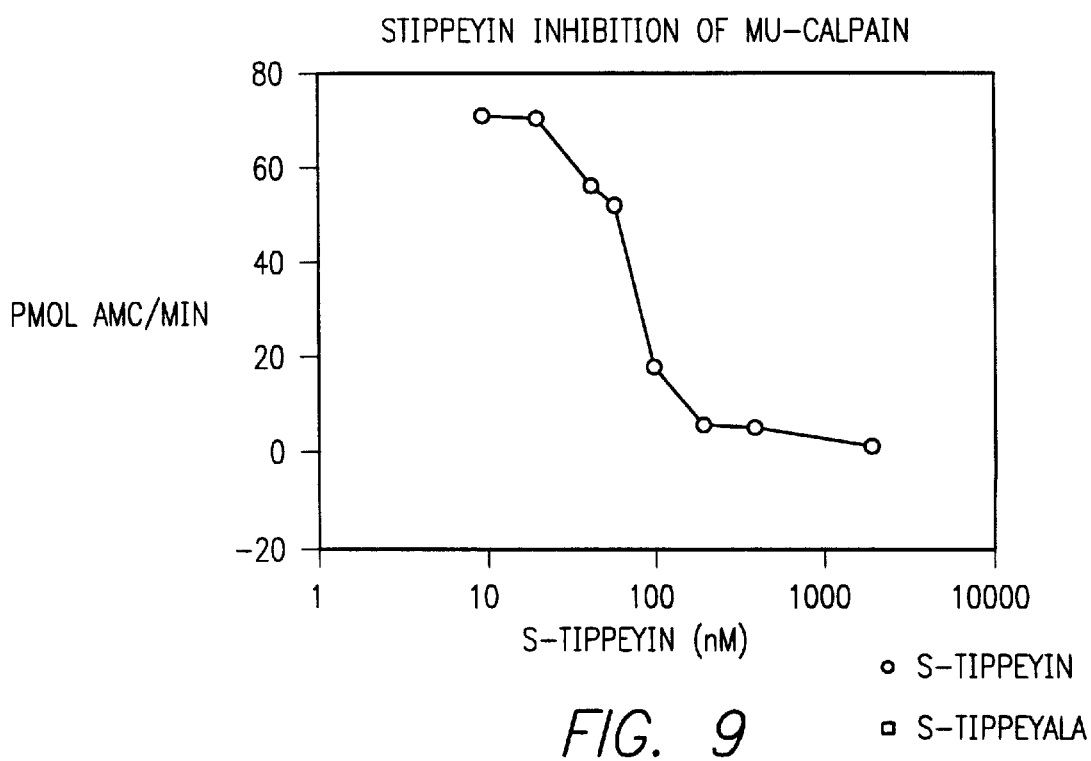
FIG. 9 is a graph showing the dose-dependent inhibition of μ-calpain by S-TIPPEYIN. S-TIPPEY-ala was used as a negative control. Suc-LLVY-AMC (SEQ ID NO:7) was used as a calpain substrate.

The assay was performed in a 0.5 ml reaction volume at 37° C. The reaction buffer contained 50 mM KCl, 10 mM Tris-HCl (pH 7.5), 1 mM EDTA, and 1 mM DTT. Two hundred µM suc-LLVY-AMC (SEQ ID NO:7) was added along with 5 mM $CaCl_2$. Calpastat or S-TIPPEY-ala was then added at the given concentrations (FIG. 9). At time zero, 4.0 µg of purified µ-calpain was added, resulting in a final concentration of 70 nM enzyme. The initial rate of AMC production was measured by fluorimetry for the first few minutes. Fluorescent excitation was at 360±2 nm and emission detection was at 460±10 nm. AMC standard solutions were used to determine moles of AMC generated from emission data. The initial rate of substrate cleavage was given as picomoles of AMC released/microgram calpain/minute.

This assay showed that calpastat inhibits µ-calpain cleavage of suc-LLVY-AMC (SEQ ID NO:7) with an $IC_{50}$ of 50 nM (FIG. 9). In contrast, S-TIPPEY-ala had no inhibitory activity in this assay even at a concentration of 10 µM.

Figure 10:
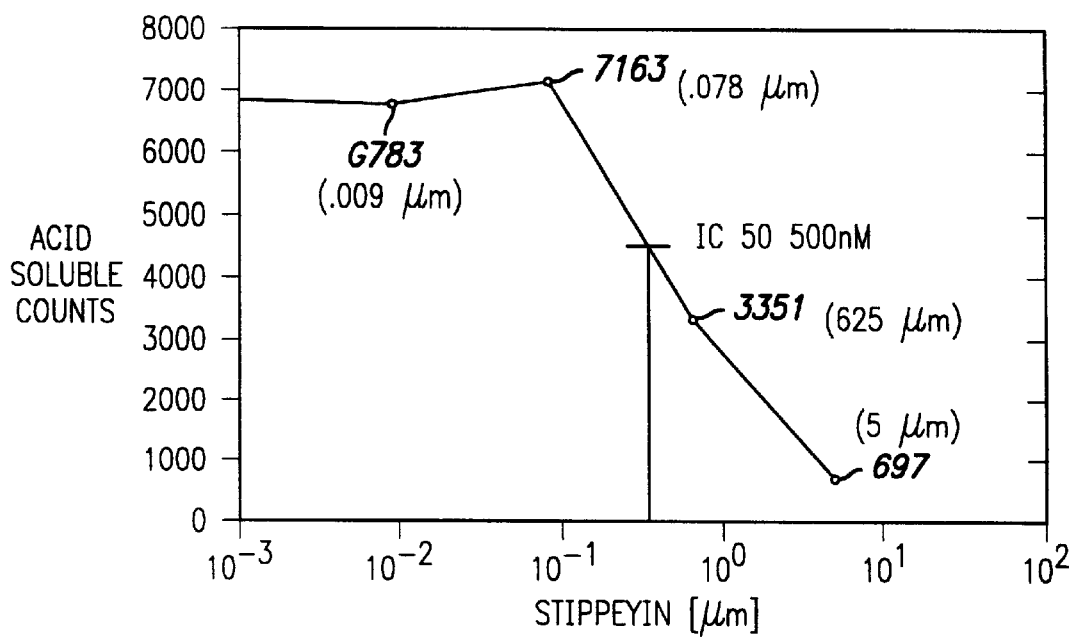
FIG. 10 is a graph showing the dose-dependent inhibition of μ-calpain by S-TIPPEYIN. [$^{14}$C]-methylcasein was used as a calpain substrate.

Another calpain inhibition assay entails measurement of the inhibition of calpain cleavage of a protein substrate methylcasein in a cell-free system. Methylcasein is a substrate of both µ- and m-calpain (see, e.g., DeMartino et al., J. Biol. Chem. 261:12047–12052, 1986; Croall et al., Physiol. Rev. 71:813–847, 1991). The assay was performed in a 0.1 ml reaction volume at 30° C. The reaction buffer contained 50 mM MOPS (pH 7.5) and 1.4 mM DTT. The substrate was added, along with 10 mM $Ca^{2+}$, to a final concentration of 0.5 mg/ml. Calpastat or S-TIPPEY-ala was added at the given concentrations (FIG. 10). Purified µ-calpain was then added to the reaction mix to give a concentration of 2.7 µM. The reaction was allowed to proceed for 10 minutes, and was stopped with 0.7 ml of 10% tricholoracetic acid containing 2 mg/ml bovine serum albumin. The reaction mix was then incubated on ice for 1 hour and centrifuged at 1,500×g for 10 minutes. Two hundred µl of the supernatant was counted for $^{14}C$ cpm in 5 ml of scintillation fluid. Calpain activity was determined by subtracting $Ca^{2+}$-independent acid soluble cpm (in the presence of EDTA) from $Ca^{2+}$-dependent acid soluble cpm (in the presence of excess $Ca^{2+}$) The $IC_{50}$ of calpastat in this assay was 500 nM.

EXAMPLE 7

Cerebral Ischemia in Rats

This example provides a protocol for determining the effectiveness of a calpastat-like fusion protein in reducing cerebral infarction in rats that have undergone ischemia surgery. This model mimics a focal ischemic episode (or "stroke").

Experimental rats are anesthetized (e.g., with chloral hydrate) prior to surgery and their body temperatures are maintained at 37±0.50° C. using a heating blanket connected to a temperature feedback monitor. The right femoral artery is cannulated with a silicon catheter for measurement of blood pressure and blood gases. Blood samples can also be obtained through the catheter and used to determine fusion protein levels in sera. The right femoral vein is similarly cannulated for infusions.

To induce ischemia, a 4-0 nylon suture with a flame-rounded tip is inserted into the right external carotid artery just distal to the right common carotid bifurcation and advanced 18.5–19.5 mm (depending on the animal's weight) through the internal/intracranial carotid arteries until the tip occludes the origin of the MCA. The suture is left in place for 2 hours and then withdrawn into the external carotid artery. Immediately following restoration of blood flow, animals are continuously infused for 3 hours with either saline (0.5 ml/hr), a calpastat-like fusion protein, or a control peptide. Arterial blood gases, pH, and hematocrit are monitored before vascular occlusion and at the end of drug infusion. Mean arterial blood pressure is measured before and during occlusion and throughout drug infusion. Blood samples for determination of the fusion protein serum levels (e.g., by Western blotting) are drawn 2.5 hours after the start of drug infusion and 30 minutes following drug termination.

To measure the extent of infarction, the rats are sacrificed 48 hours after the onset of occlusion and cerebral infarct volume is determined by computer image analysis of coronal brain slices stained with 2% 2,3,5-triphenyltetrazolium chloride (BIOQUANT, R+M Biometrics, Nashville Tenn). Infarct volume is calculated using the "indirect" method, in which the infarcted area of a brain slice is first determined by subtracting the undamaged area of ipsilateral hemisphere from the total area of the contralateral hemisphere (Swanson et al., *J. Cereb. Blood Flow Metab.* 10:290–293, 1990). The infarcted area is then multiplied by section thickness (2 mm) to obtain infarct volume for that slice. Total brain infarct volume is finally obtained by summing the volumes of the series of seven brain slices prepared from each animal. Statistical analysis of treatment groups is performed using one-way ANOVA followed by a two-tailed unpaired t-test.

EXAMPLE 8

Treatment of Alzheimer's Disease

Calpastat-like fusion proteins can be used to treat Alzheimer's disease and brain aging. Fusion proteins can be tested using a murine model of Alzheimer's disease (see, e.g., Games et al., *Nature* 373:523–27, 1995; Sisk et al., *J. Neurosci.* 16:5795–5811, 1996; Irizarry et al., *J. Neurosci.* 17:7053, 1997; Johnson-Wood et al., *Proc. Natl. Acad. Sci. USA* 94:1550–1555, 1997).

EXAMPLE 9

Treatment of Cataracts

Calpastat-like fusion proteins can be used to treat cataracts. The fusion proteins can be screened for effectiveness using animal models of cataract disease (see, e.g., Zigler, *Exp. Eye Res.* 50:651–657, 1990; Shearer et al., *Current Eye Res.* 6:289–300, 1987).

EXAMPLE 10

Treatment of Sickle Crisis

Calpastat-like fusion proteins can be used to treat sickle crisis. The fusion proteins can be screened for effectiveness using animal models of sickle cell disease (see, e.g., Ryan et al., *Science* 278:873–876, 1997; Paszty et al., *Science* 278:876–878, 1997).

EXAMPLE 11

Treatment of Inflammatory Disorders

Figure 11:
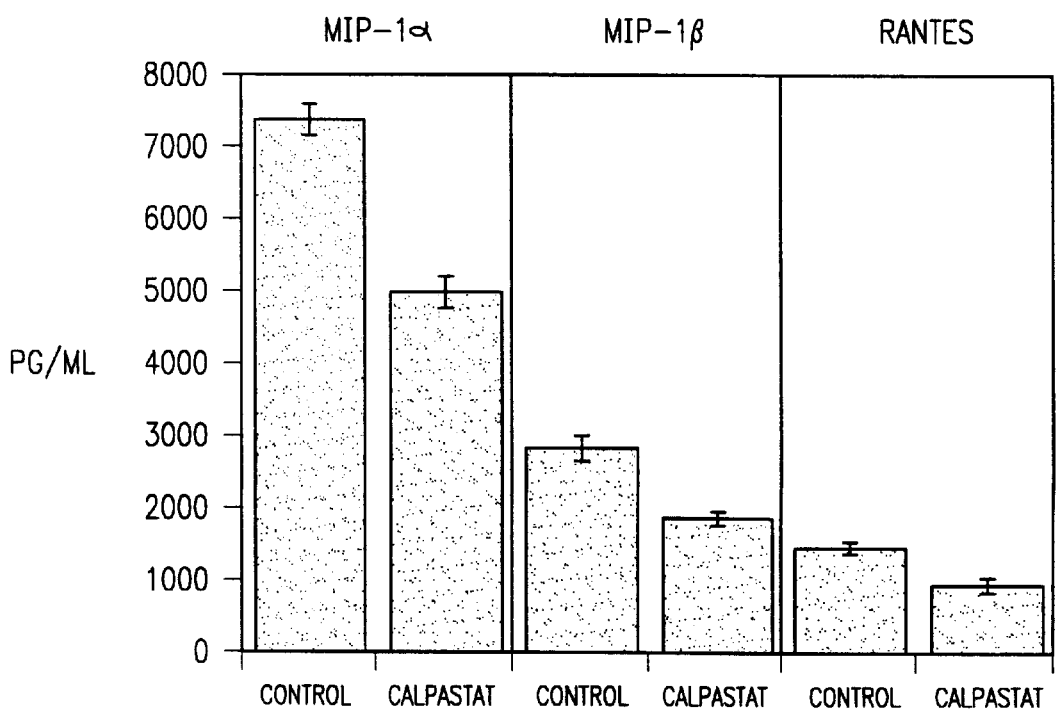
FIG. 11 is a graph depicting the effect of calpastat (S-TIPPEYIN) on chemokine production of thapsigargin stimulated (4 nM) U937 cells.

Calpastat-like peptides can inhibit chemokine production in vitro. The effect of calpastat on chemokine production was tested as follows. Samples of thapsigargin-stimulated U937 cells were incubated with 5 nM calpastat or control buffer. The chemokines (MIP-1α, MIP-1P and RANTES) in the supernatants of U937 cells were assayed using Quantikine™ kits and as described by R&D Systems (Minneapolis, Minn.). FIG. 11 depicts the results of these experiments and shows that calpastat incubation reduced the production of all three chemokines by about one third. Thus, calpastat can be used to reduce production of inflammatory cytokines and treat inflammatory disorders.

Calpastat-like fusion peptides (e.g., those including the peptides shown in Table 1) can be used to treat inflammatory disorders including, but not limited to, rheumatoid arthritis, skin inflammation (e.g., polyarteritis nodosa), glomerulonephritis, asthma, pneumonitis (e.g., pneumonitis and pulmonary eosinophilia), and uveltis. Calpastat can significantly inhibit chemokine production (and thereby inhibit inflammatory processes) at concentrations below those required to substantially inhibit platlet activation.

One of the animal models that can be used to examine the effect of calpastat-like fusion peptides on inflammation is the rabbit model of hemorrhagic vasculitis described by Argenbright and Barton (*J. Clin. Invest.* 89:259–72, 1992).

EXAMPLE 12

Immunosuppression

Inhibitors of calpain, including calpastat, can be used as immunosuppressants. Accordingly, calpastat-like fusion proteins can be used to treat graft-vs-host disease; to otherwise reduce the risk of transplant rejection (e.g., renal transplant rejection, cardiac transplant rejection, liver transplant rejection); and to treat other conditions associated with an unwanted immune response (e.g., autoimmune diseases). Thus, calpastatin-like fusion peptides (or gene constructs encoding those peptide) can be administered to treat autoimmune diseases such as non-obese diabetes, systemic lupus erythematosus, sclerodermia, Sjögren's syndrome, dermatomyositis or multiple sclerosis, rheumatoid arthritis, artheriosclerosis, and psoriasis, asthma, rhinitis, fibrosis, chronic bronchitis, hepatitis, post-infectious anergy, acquired immune deficiency diseases such as AIDS, and post traumatic immunological anergy.

EXAMPLE 13

Platelet Storage

Currently, platelets cannot readily be stored in the cold. For example, platelets in citrate dextrose plasma (CDP) undergo an irreversible disk-to-sphere transition when they are stored in the cold, which results in loss of viability following transfusion. Moreover, platelets can be stored for only about five days in CDP due to growth of contaminating bacteria. As a result, many units of platelets are discarded.

Calpastat-containing fusion peptides can be used to protect platelets from the disk-to-sphere shape change and thereby improve platelet viability.

Figure 12:
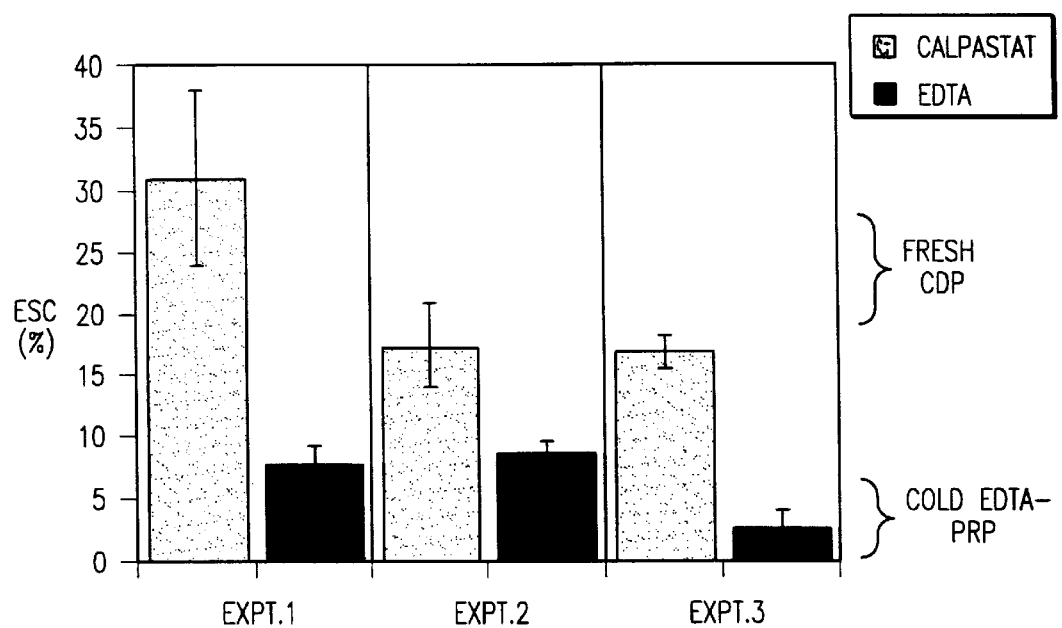
FIG. 12 is a graph depicting the effect of calpastat on platelet shape change after 24 hours of cold storage (ESC= extent of shape change).

To examine the effects of calpastat on shape change, platelet rich plasma (PRP) was preincubated with calpastat (50 mM) or EDTA for about 24 hours at 4° C. Disk-to-sphere shape change was then assayed using the extent of shape change (ESC) assay (Holme et al., *Transfusion* 38:31–40, 1998). Briefly, samples of stored PRP were treated to induce disk-to-sphere shape change by cold storage and the addition of EDTA (to prevent aggregation). ADP was then added as a stimulus to measure ESC, and shape change was measured by determining light transmission through the sample. If the initial storage conditions caused considerable disk-to-sphere shape change, there would be little additional shape change upon addition of EDTA and ADP. Conversely, if the initial storage conditions caused little disk-to-sphere shape change, there would be considerable additional shape change upon addition of EDTA and ADP. The results of three experiments in which 24 hour storage of platelets at 4° C. was tested, in the presence and absence of calpastat, are shown in FIG. 12. The bracket labelled "fresh CDP" indicates the ESC that can be expected for fresh PRP in CPD, and the bracket marked "cold EDTA-treated PRP" indicates the ESC that can be expected for PRP subjected to cold storage in EDTA. As FIG. 12 shows, calpastat significantly improved cold storage of PRP compared to EDTA (ESC is greater upon addition of EDTA and ADP for calpastat treated cells than non-treated cells).

Figure 13:
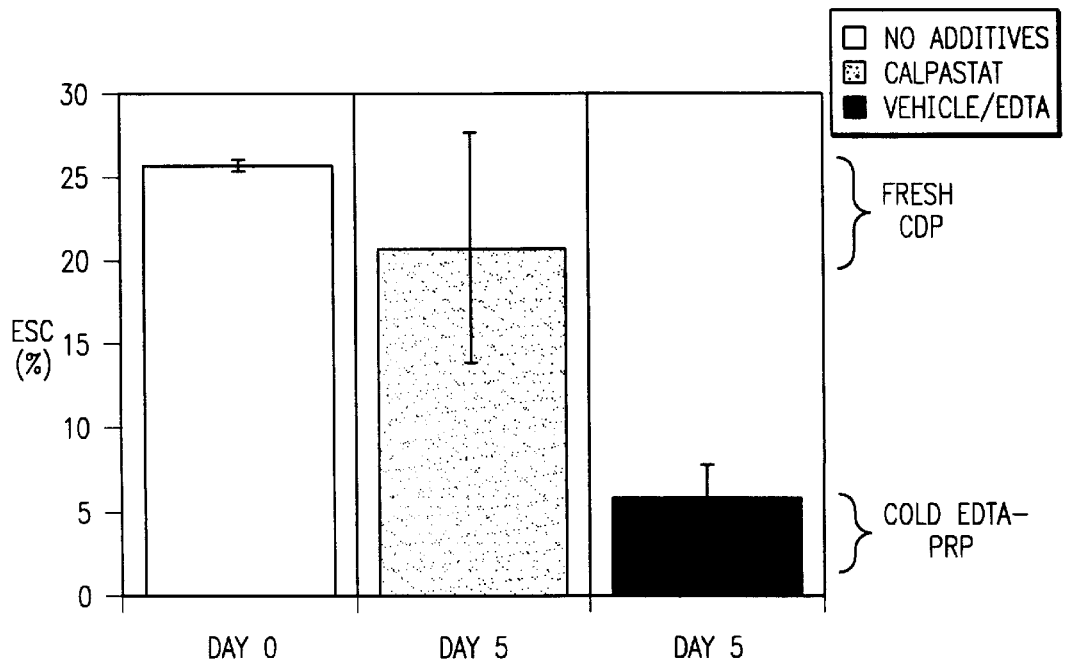
FIG. 13 is a graph depicting the effect of calpastat on platelet shape change after 5 days of cold storage.

FIG. 13 shows the results of an ESC assay performed on PRP stored at 4° C. for five days in the presence of calpastat or control vechicle/EDTA. The day O control is an assay performed on fresh PRP with no cold storage in standard buffer. Calpastat provided considerable protection against disk-to-sphere shape change even after five days of cold storage.

Because calpastat is a reversible inhibitor of calpain and platelet activation and because calpastat can be washed out of platelets, allowing them to aggregate in the presence of thrombin, calpastat and related calpain inhibitors are useful for preservation of platelets in the cold.

EXAMPLE 14
Inhibition of Platelet Activation on Surfaces

Platelet activation on surfaces is a major problem in many different medical procedures (e.g., angioplasty, cardiopulmonary bypass, extracorporeal oxygenation, and dialysis).

Figure 14A:
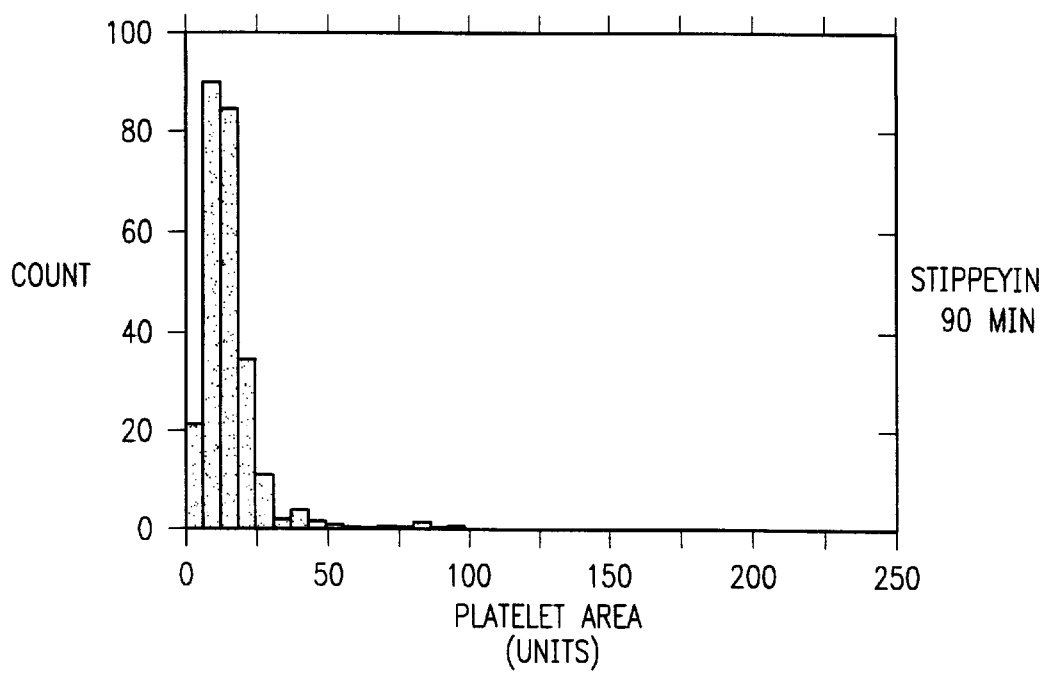
FIGS. 14A and 14B are graphs depicting the effect of S-TIPPEYIN and S-TIPPEY-ala, respectively, on platelet spreading.
Figure 14B:
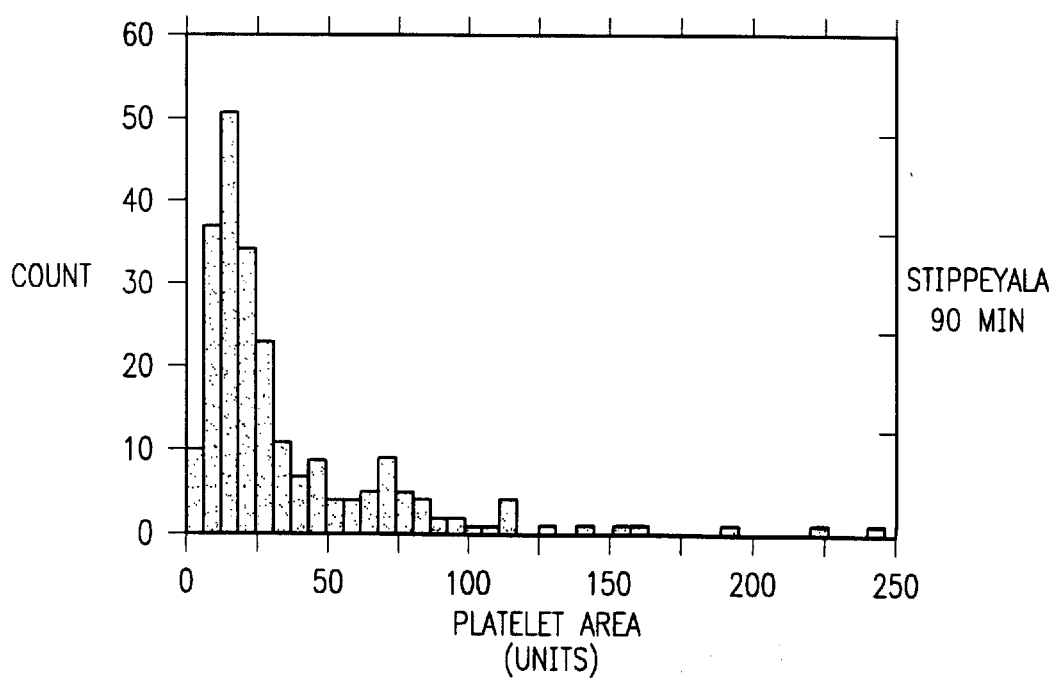

Platelet activation on surfaces can be inhibited by calpastat or calpastat-like fusion proteins. To study the effect of calpastat on platelet activation on surfaces, platelets were preincubated with 100 mM calpastat (S-TIPPEYIN) or S-TIPPEY-ala for 90 minutes at 37° C. The platelets were then spread on glass surfaces for 20 minutes, and then fixed. Platelet spreading was assayed by Oregon Green-phalloidin staining, followed by fluorescence micrography. FIG. 14A depicts the distribution of platelet spread size in the presence of S-TIPPEYIN, and FIG. 14B depicts the distribution platelet spread size in the presence of S-TIPPEYIN-ala. Calpastat (S-TIPPEYIN) pretreatment resulted in a 70% reduction in spreading on the glass surface.

In a related series of experiments, gel filtered platelets were preincubated with either calpastat or calpastat-ala (100 $\mu$M concentrations for 30, 60, and 90 minutes at 37° C.) or with the low molecular weight inhibitors calpeptin, MDL, or E64d (50–500 $\mu$M for 10 minutes at 37° C.). An aliquot of the platelet suspension (80 $\mu$l) was plated on a glass coverslip and the platelets were allowed to settle and spread for 20 minutes at 37° C. in a tissue culture incubator (Revco Ultima™ Incubator; Revco Scientific, Inc., Asheville, N.C.). The platelets were then fixed in 3.7% formaldehyde, permeabilized with Triton X-100 (0.1% for four minutes), and blocked in PIPES buffered saline with 3% bovine serum albumin. The coverslips were stained with Oregon-Green-phalloidin and photographed on Kodak Tri-X film by photomicrography using a Nikon Optiphot 2 fluorescence microscope (100×objective). The cellular area of spread platelets was determined by computer assisted image analysis using NIH Image 1.61.

Treatment of platelets with 3% DMSO led to a complete inhibition of spreading and provided baseline cell area for unspread platelets. Percent inhibition of spreading was calculated from the increase in mean cell area for untreated and treated samples vs. unspread DMSO controls.

Figure 17:
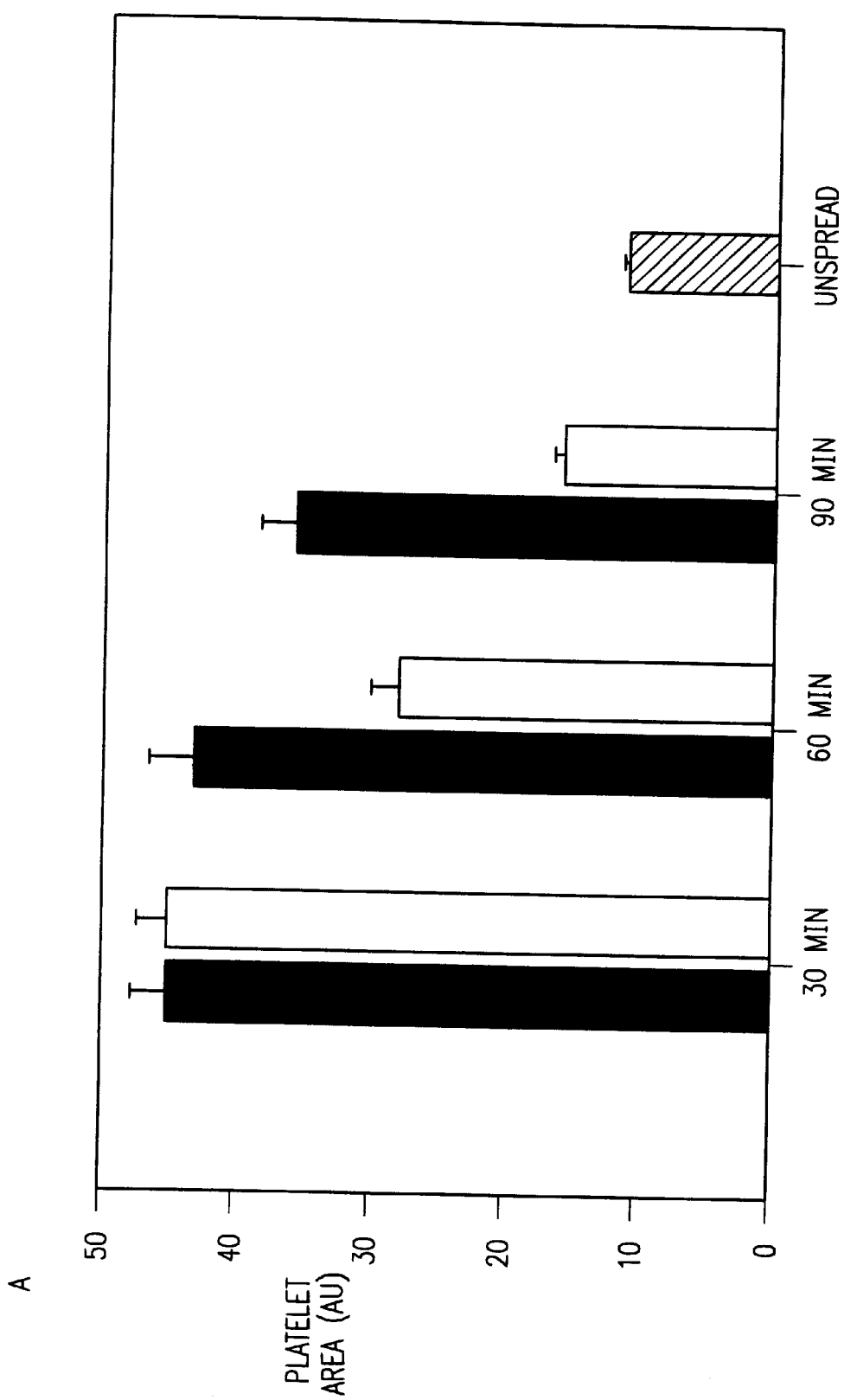
FIG. 17 is a bar graph illustrating calpastat inhibition of platelet spreading. Platelet area is presented in AUs (area units), with one AU being 0.625 $\mu m^2$.

Pre-incubation of platelets with calpastat (100 $\mu$M) for 30, 60, or 90 minutes resulted in 0, 46, or 80% inhibition of platelet spreading (i.e., increase in mean platelet area), respectively, relative to the calpastat-ala control (FIG. 17). Calpastat-ala results in minimal inhibition of platelet actin remodeling, including filopodial and lamellipodial protrusion formation. Thus, the calpastatin motif is responsible for inhibition of spreading. Moreover, the extent of inhibition depends on the pre-incubation time and 30–60 minutes is required. Calpastat does not act as rapidly as the peptidyl calpain inhibitors calpeptin, MDL, and E64d. In contrast, ZLLYCHN$_2$, which takes up to 14 hours to inhibit spreading in fibroblasts, has no inhibitory activity in this assay. The IC$_{50}$ of calpastat for inhibition of platelet spreading is 35 $\mu$M.

Notably absent in the calpastat-treated cells is the peripheral rim of F-actin, which otherwise appears at the leading edge of each lamellae. Half of the platelets pre-treated with calpastat (100 $\mu$M) for 1.5 hours are round and unspread on glass. The disc-like, unspread platelets demonstrate no (or few) filopodia and lack lamellipodial protrusions. These findings suggest that calpain is involved in an early process in spreading, rather than in retraction following spreading (the unspread platelets lack the pattern of retraction fibers together with extended filopodia that are seen in platelets undergoing cytoskeletal retraction).

To confirm the role of calpain in platelet spreading, the peptidyl calpain inhibitors calpeptin, MDL, and E64d were tested for their ability to inhibit spreading. Platelets were pre-incubated for 10 minutes with varying concentrations of calpeptin, MDL and E64d (50–500 $\mu$M) and then spread on glass, as described above. All three compounds effectively inhibited platelet spreading (Table 3). The IC$_{50}$s for inhibition of spreading by calpeptin, MDL, and E64d are 200, 200, and >250 $\mu$M, respectively (Table 3). These concentrations are at least 6-fold higher than the IC$_{50}$ of calpastat.

TABLE 3

| Inhibitor | IC$_{50}$ ($\mu$M) |
|---|---|
| Calpastat | 35 |
| Calpastat-ala | NI |
| Calpeptin | 200 |
| MDL | 200 |
| E64d | >250 |
| NH$_4$Cl (10 mM) | NI |

The spreading morphology of platelets treated with peptidyl calpain inhibitors is similar to that of calpastat-treated platelets. Regardless of the inhibitor, there was a notable absence of the peripheral rim of F-actin at the leading edges of the lamellae. Under these conditions (spreading on glass, as described above), 30% of platelets pre-treated at the IC$_{50}$ for calpeptin or MDL (200 $\mu$M) are round and unspread, with a thin cortical layer of F-actin. As occurs with calpastat treatment, the unspread platelets have no (or few) filopodia and lack lamellipodia. About 20% of the platelets pretreated at the IC$_{50}$ of E64d (250 $\mu$M) are round and unspread.

Inhibition of platelet spreading by peptidyl calpain inhibitors does not occur through inhibition of lysosomal cathepsins because treatment with 10 mM NH$_4$Cl has no effect on platelet spreading (Table 3).

To prevent platelet spreading on a surface, calpastat, a related calpain inhibitor, or a calpastat-like fusion protein would be attached to the surface non-covalently, for example, in a polyethylene glycol (PEG) material, without loss of function. The proteins could also be attached covalently to surfaces by conservative substitution of the lysine residues with arginine (except for the last residue), with subsequent N-hydroxysuccinamide ester chemistry used to attach the inhibitor to surfaces via aliphatic linker arms.

The inhibitor(s) could be applied to stents (e.g., those used for angioplasty), tubing (e.g., cardiopulmonary bypass tubing or dialysis tubing), oxygenation devices, catheters (e.g., those used for angiographic procedures, Swan-Ganz catheters, Hickman catheters, or Vascath catheters), Gortex vascular prostheses, and artificial heart valves.

EXAMPLE 15
Cloning of a Calpastat Minigene

Figure 18A:
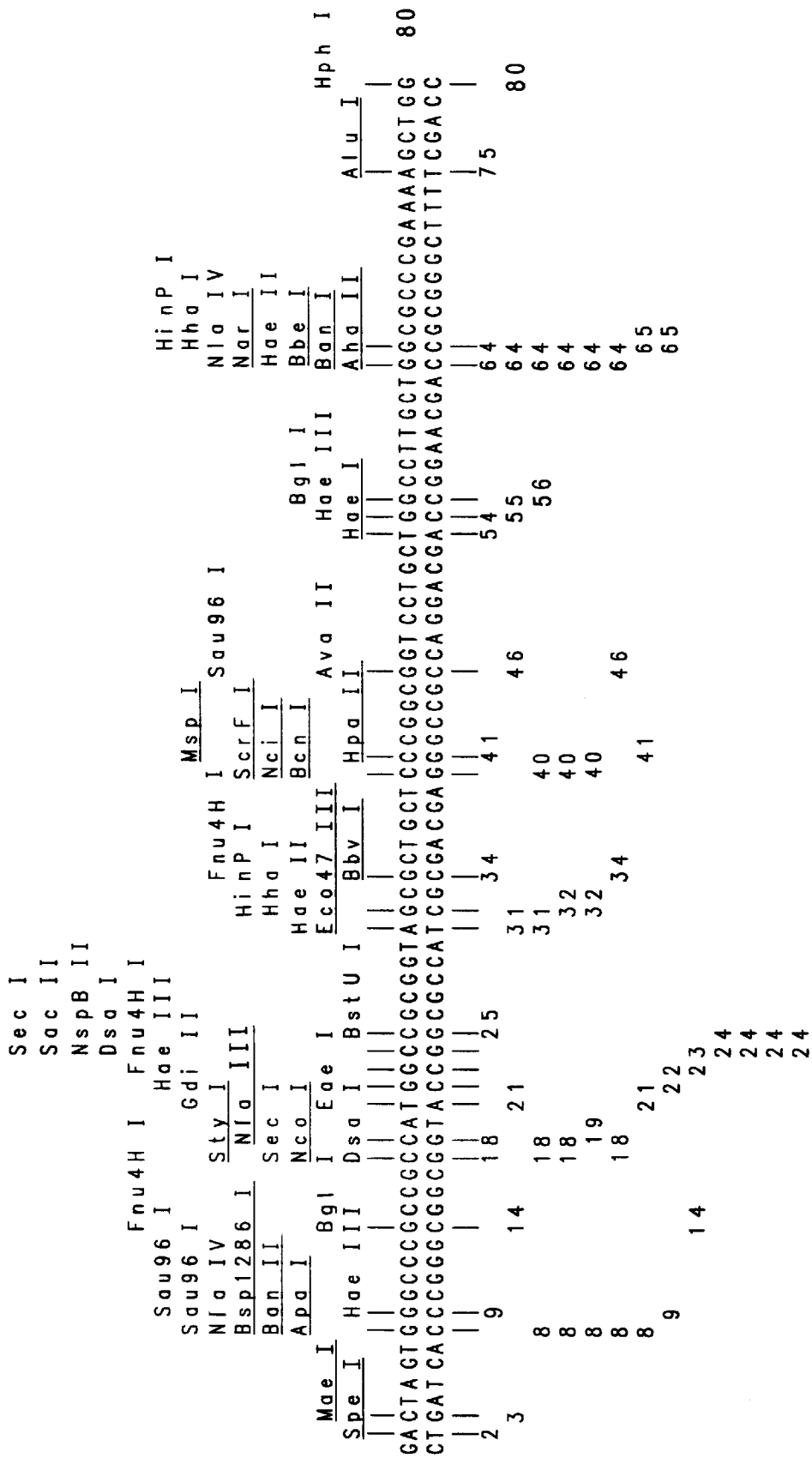
FIG. 18 is a schematic representation of a nucleic acid fragment generated by PCR (top strand, SEQ ID NO:18; bottom strand, SEQ ID NO:19). The construct encodes Met-calpastat.
Figure 18B:
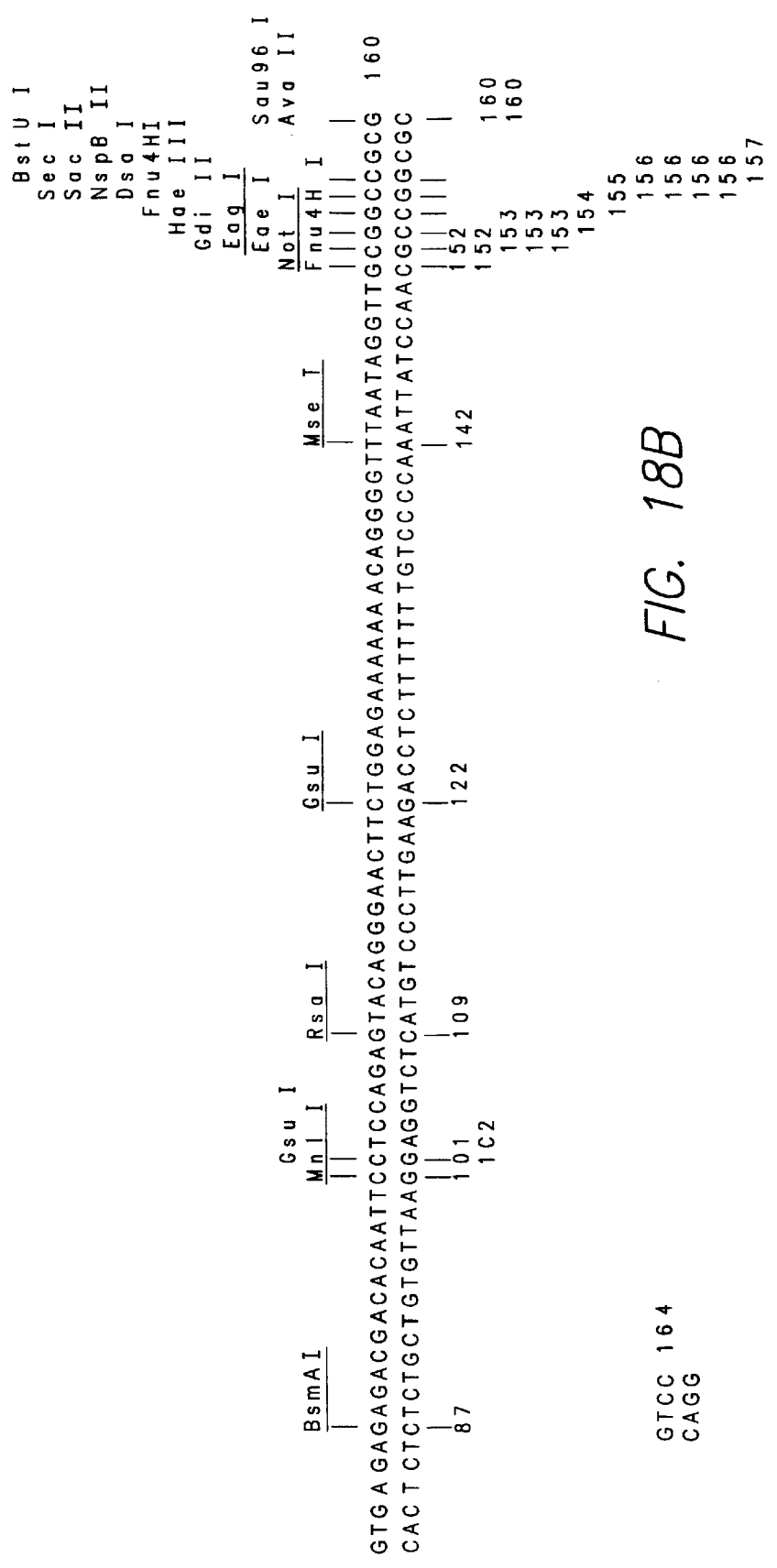

A polymerase chain reaction (PCR) product, 160 basepairs in length, that encodes the Met-calpastat gene therapy construct has been generated and gel-purified. This construct encodes a calpastat molecule, Met-calpastat, which has an amino-terminal methionine (FIG. 18). TOPO™ cloning (Invitrogen, Carlsbad, Calif.) will be used to insert the PCR product into a suitable eukaryotic expression vector polylinker. pRC/CMV or pcDNA3 (Invitrogen, Carlsbad, Calif.) are suitable vectors. The polylinker insert containing the Met-calpastat minigene can then be inserted into any of the naked DNA or viral gene therapy systems indicated below.

TOPO™ TA Cloning kits available from Invitrogen (Carlsbad, Calif.) provide a highly efficient and rapid cloning strategy for the direct insertion of Taq polymerase-amplified PCR products into a plasmid vector. No ligase, post-PCR procedures, or PCR primers containing specific sequences are required. The Invitrogen product literature provides an excellent description of this procedure, should further explanation be desired.

EXAMPLE 16
Production of Calpastat in Eukaryotic or Bacterial Cells

A DNA sequence that can be used to express calpastat is shown in FIG. 15. The sequence encodes a polypeptide that contains an amino-terminal methionine, which is hydrophobic and does not interfere with the membrane penetrating function of signal sequences. However, the polypeptide can be produced without the intial methionine using various techniques known to those of skill in the art. Generally, these techniques produce a polypeptide with an initial methionine and then remove it.

Because the signal peptidase cleavage site of the kFGF signal sequence is deleted, calpastat should be secreted intact, which would facilitate purification from eukaryotic tissue culture supernatants or bacterial growth medium. For bacterial expression, the calpastat or calpastatin sequence could be inserted in an IPTG-regulated expression vector. For eukaryotic expression, the calpastat or calpastatin sequence could be inserted in a tetracycline-induced expression vector system.

Thus, the invention encompasses nucleic acid molecules that encode calpastat-like fusion peptides (e.g., a peptide shown in Table 1 fused to a suitable cell penetration peptide). The nucleic acid molecules can be inserted into vectors, such as those described below, which will facilitate expression of the gene. Accordingly, expression vectors containing such nucleic acid molecules and cells transfected with these vectors are within the scope of the invention.

A transformed cell is any cell into which (or into an ancestor of which) a nucleic acid molecule encoding a polypeptide of the invention has been introduced (e.g., by recombinant DNA techniques).

An isolated nucleic acid molecule is a nucleic acid molecule that is separated from the 5' and 3' coding sequences with which it is immediately contiguous in the naturally occurring genome of an organism. Isolated nucleic acid molecules include nucleic acid molecules which are not naturally occurring, e.g., nucleic acid molecules created by recombinant DNA techniques. Nucleic acid molecules include both RNA and DNA, including cDNA and synthetic DNA (i.e., chemically synthesized DNA).

The expression systems that can be used to produce calpastatin-like fusion proteins include, but are not limited to, microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, Saccharomyces and Pichia) transformed with recombinant yeast expression vectors containing the nucleic acid molecules of the invention; insect cell systems infected with recombinant virus expression vectors (for example, baculovirus); or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter).

In bacterial systems, a number of expression vectors may be advantageously selected depending upon the use intended for the gene product being expressed. Such vectors include, but are not limited to, the *E. coli* expression vector pUR278 (Ruther et al., *EMBO J*. 2:1791, 1983), in which the coding sequence of the insert may be ligated individually into the vector in frame with the lacZ coding region so that a fusion protein is produced; pIN vectors (Inouye and Inouye, *Nucleic Acids Res.* 13:3101–3109, 1985; Van Heeke and Schuster, *J. Biol. Chem.* 264:5503–5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) can be used as a vector to express foreign genes. The virus grows in *Spodoptera frugiperda* cells (for example, see Smith et al., *J. Virol.* 46:584, 1983; Smith, U.S. Pat. No. 4,215,051).

In mammalian host cells, a number of viral-based expression systems can be utilized. In cases where an adenovirus is used as an expression vector, the nucleic acid molecule of the invention can be ligated to an adenovirus transcription/translation control complex, for example, the late promoter and tripartite leader sequence. This chimeric gene can then be inserted in the adenovirus genome by in vitro or in vivo recombination.

Specific initiation signals may also be required for efficient translation of inserted nucleic acid molecules. These signals include the ATG initiation codon and adjacent sequences. The initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516–544, 1987).

In addition, a host cell strain may be chosen that modulates the expression of the inserted sequences, or modifies and processes the gene product in the specific fashion desired. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used.

Expression contructs capable of expressing calpastat, calpastat related calpain inhibitors, or calpastat-like fusion proteins can be prepared using methods known to those of ordinary skill in the art. Such constructs can be used for gene therapy, for example, for paracrine production of calpastat at a site of inflammation, within a tumor or within the vicinity of potential cancer cell movement, or at the site of an angioplasty. A DNA sequence encoding a calpastat related calpain inhibitor containing the human calpastatin repeat 1 sequence is shown in FIG. 16.

EXAMPLE 17
Treatment of Cancer

Calpastatin, related calpain inhibitors, and calpastat-like fusion peptides can be used to inhibit the motility of cancer cells, which would in turn inhibit their ability to spread to other tissues or parts of the body, as well as the survival of cancer cells. Without any intention to limit the invention to proteins that function by any particular mechanism, it is believed that calpastatin, related inhibitors, and calpastat-like proteins inhibit actin remodeling.

Calpastatin, related inhibitors, and calpastat-like fusion proteins can be administered in a variety of ways to a patient who has cancer. For example, calpastat-like fusion proteins can be delivered via a liposomal delivery system that selectively targets tumor cells. Such delivery systems are known in the art, and are not limited to use for the treatment of cancer; liposomal delivery systems can be used to administer calpastatin, related inhibitors, and calpastat-like fusion proteins to treat the other conditions described herein (e.g., sickle cell crisis, HIV infection, cerebral ischemia, Alzheimer's Disease, cataracts, inflammatory disorders, and disorders or conditions in which immunosuppression is required). For example, the pegylated stealth liposome system, which has been used to deliver doxorubicin (Vail et al., *Clinical Cancer Res.* 4:1567–71, 1998) to cancer cells could be used. The compositions of the invention could be delivered alone, in combination, or together with chemotherapeutic agents. Because calpastat can be secreted intact with its signal sequence, and can act in a paracrine fashion, it is an ideal candidate for gene therapy applications. Again, the application of calpastatin, related inhibitors, and calpastat-like fusion proteins via gene therapy is not restricted to any particular type of disease or condition. Gene therapy can be employed in any situation in which calpastatin, related inhibitors, or calpastat-like fusion proteins are effectively administered.

Without limiting the invention to calpastat-like fusion proteins that function by a particular mechanism, it is believed that calpastatin, like other protease inhibitors, may block the degradation of wild type p53 and thereby promote apoptosis of cancerous cells (see, e.g., Pariat et al., *Mol. and Cell. Biol.* 17:2806–2815, 1997; Zhang et al., *Oncogene* 14:255–263, 1997; Braun et al., *Int. J. Cancer (Pred. Oncol)* :84:6–9, 1999; Kimura et al., *Nature Medicine* 4:915–922, 1998; and Zhu et al., *Biochem. & Biophys. Res. Com.* 214:1130–1137, 1995).

Because the calpastatin-like fusion peptides of the invention can inhibit calpains that are ubiquitously expressed, these peptides can be used to inhibit the motility or reduce the survival of numerous types of cancer cells. For example, calpastatin-like fusion peptides can be used to treat cancers of mesenchymal origin such as sarcoma, e.g., fibrosarcoma, myxosarcoma, liposarcoma, chondrosarcoma, osteogenic sarcoma or chordosarcoma, angiosarcoma, endotheliosarcoma, lymphangiosarcoma, synoviosarcoma or mesothelioma; leukemias and lymphomas such as acute myelogenous leukemia (AML), acute lymphocytic leukemia (ALL), chronic myelogenous leukemia (CML), myelodysplastic syndrome (MDS), chronic lymphocytic leukemia, prolymphocytic leukemia, Non-Hodgkin's lymphoma, AIDS-related lymphoma, Kaposi's sarcoma, multiple myeloma, Hodgkin's disease; sarcomas like leiomyosarcoma or rhabdomyosarcoma, tumours of epithelial origin (carcinomas) such as squamous cell carcinoma, basal cell carcinoma, sweat gland carcinoma, sebaceous gland carcinoma, esophagel carcinoma, gastric carcinoma, breast carcinoma, colon adenocarcinoma, pancreatic adenocarcinoma, adenocarcinoma of the thyroid, papillary carcinoma, papillary adenocarcinoma, cystadenocarcinoma, medullary carcinoma of the thyroid, undifferentiated carcinoma, non-small cell lung carcinoma, small cell lung carcinoma, bronchogenic carcinoma, melanoma, renal cell carcinoma, hepatoma-liver cell carcinoma, bile duct carcinoma, cholangiocarcinoma, papillary carcinoma, transitional cell carcinoma choriocarcinoma, semonoma or embryonal carcinoma, prostate, uterine, or ovarian carcinomas, or other carinomas of the reproductive tract, bladder carcinoma, squamous cell carcinoma of the neck and head region, and tumours of the central nervous system like glioma, meningoma, medulloblastoma, schwannoma or ependymoma.

EXAMPLE 18
Treatment of Restenosis in Angioplasty

Introduction of calpastat, a related calpain inhibitor, or a calpastat-like fusion peptide at the time of angioplasty can potentially have a lasting effect on restenosis. The peptide could be introduced at the time of angioplasty by catheter, balloon, or stent. A gene therapy vector could also be included, for later expression, beginning about one day following the procedure.

OTHER EMBODIMENTS

It is to be understood that while the invention has been described in conjunction with the detailed description thereof, that the foregoing description is intended to illustrate and not limit the scope of the invention, which is defined by the scope of the appended claims. For example, the fusion proteins may be used to inhibit activation of NF-κB regulated viruses, for example, cytomegaloviruses, hepatitis B virus, herpes viruses, adenoviruses, HTLV-I, Sendai virus, human herpes virus 6, and HSV type 1 (see, e.g., Baeuerle, *Biochem. Biophys. ACTA* 1072:63–80, 1991).

Other aspects, advantages, and modifications are within the scope of the following claims.

What is claimed is:

1. A method of inhibiting the motility or survival of a cancer cell, the method comprising contacting the cell with an effective amount of fusion protein having a first portion and a second portion, the first portion comprising a signal sequence capable of delivering the fusion protein into the cell and the second portion comprising a calpastatin peptide comprising the sequence Xaa-Xaa-Leu-Gly-Xaa-Xaa-Xaa-Xaa-Thr-Ile-Pro-Pro-Xaa-Tyr-Xaa-Xaa-Leu-Leu-Xaa-Xaa-Xaa-Xaa-Xaa-Xaa (SEQ ID NO:4), wherein Xaa at position 1 is Glu, Asp, or Lys;

Xaa at position 2 is Lys, Glu, Ala, or Asn;

Xaa at position 5 is Glu, Lys, or Ile

Xaa at position 6 is Arg, Lys, or Asp;

Xaa at position 7 is Asp, or Glu;

Xaa at position 8 is Asp, Val, Ser, Gly, or Glu;

Xaa at position 13 is Glu, Lys, or Asp;

Xaa at position 15 is Arg, Lys, or Gln;

Xaa at position 16 is Glu, His, Lys, or Leu;

Xaa at position 19 is Glu, Asp, Asn, Ala, or Val;

Xaa at position 20 is Lys, Asp, Gln, Asn, Thr, or Met;

Xaa at position 21 is Lys, Asp, Glu, Gly, or Asn;

Xaa at position 22 is Thr, Glu, Gly, or Lys;

Xaa at position 23 is Gly, Ala, Glu, Gln, Lys or Asp; and

Xaa at position 24 is Val, Ile, Asp or Gly.

2. The method of claim 1, wherein the amino-terminal end of the second portion is covalently bonded to the carboxy-terminal end of the first portion by a peptide bond.

3. The method of claim 1, wherein the first portion has the sequence of SEQ ID NO:3.

4. The method of claim 1, wherein the fusion protein has the sequence of SEQ ID NO:1.

5. The method of claim 1, wherein the calpastatin peptide comprises the sequence of SEQ ID NO:8.

6. The method of claim 1, wherein the calpastatin peptide comprises the sequence of SEQ ID NO:11.

7. The method of claim 1, wherein the calpastatin peptide comprises the sequence of SEQ ID NO:12.

8. The method of claim 1, wherein the calpastatin peptide comprises the sequence of SEQ ID NO:13.

9. The method of claim 1, wherein the calpastatin peptide comprises the sequence of SEQ ID NO:14.

10. The method of claim 1, wherein the calpastatin peptide comprises the sequence of SEQ ID NO:15.

11. The method of claim 1, wherein the calpastatin peptide comprises the sequence of SEQ ID NO:16.

12. The method of claim 1, wherein the calpastatin peptide comprises the sequence of SEQ ID NO:17.

13. The method of claim 1, wherein the Xaa at position 1 is Glu.

14. The method of claim 1, wherein the Xaa at position 2 is Lys.

15. The method of claim 1, wherein the Xaa at position 5 is Glu.

16. The method of claim 1, wherein the Xaa at position 6 is Arg.

17. The method of claim 1, wherein the Xaa at position 7 is Asp.

18. The method of claim 1, wherein the Xaa at position 8 is Asp.

19. The method of claim 1, wherein the Xaa at position 13 is Glu.

20. The method of claim 1, wherein the Xaa at position 15 is Arg.

21. The method of claim 1, wherein the Xaa at position 16 is Glu.

22. The method of claim 1, wherein the Xaa at position 19 is Glu.

23. The method of claim 1, wherein the Xaa at position 20 is Lys.

24. The method of claim 1, wherein the Xaa at position 21 is Lys.

25. The method of claim 1, wherein the Xaa at position 22 is Thr.

26. The method of claim 1, wherein the Xaa at position 23 is Gly.

27. The method of claim 1, wherein the Xaa at position 24 is Val.

28. The method of claim 1, wherein the calpastatin peptide comprises the sequence Glu-Lys-Leu-Gly-Glu-Arg-Asp-Asp-Thr-Ile-Pro-Pro-Glu-Tyr-Arg-Glu-Leu-Leu-Glu-Lys-Lys-Thr-Gly-Val (SEQ ID NO:4).

29. The method of claim 1, wherein the first portion has the sequence of SEQ ID NO:6.

\* \* \* \* \*

SEQUENCE LISTING

<160> NUMBER OF SEQ ID NOS: 23

<210> SEQ ID NO 1
<211> LENGTH: 40
<212> TYPE: PRT
<213> ORGANISM: Eukaryote

<400> SEQUENCE: 1

Ala Ala Val Ala Leu Leu Pro Ala Val Leu Leu Ala Leu Leu Ala Pro
 1               5                  10                  15

Glu Lys Leu Gly Glu Arg Asp Asp Thr Ile Pro Pro Glu Tyr Arg Glu
             20                  25                  30

Leu Leu Glu Lys Lys Thr Gly Val
         35                  40

<210> SEQ ID NO 2
<211> LENGTH: 40
<212> TYPE: PRT
<213> ORGANISM: Eukaryote

<400> SEQUENCE: 2

Ala Ala Val Ala Leu Leu Pro Ala Val Leu Leu Ala Leu Leu Ala Pro
 1               5                  10                  15

Glu Lys Leu Ala Glu Arg Ala Asp Ala Ala Pro Glu Ala Ala Glu
             20                  25                  30

Leu Leu Glu Lys Lys Thr Gly Val
         35                  40

<210> SEQ ID NO 3
<211> LENGTH: 16
<212> TYPE: PRT
<213> ORGANISM: Artificial Sequence
<220> FEATURE:
<223> OTHER INFORMATION: synthetically generated peptide

<400> SEQUENCE: 3

Ala Ala Val Ala Leu Leu Pro Ala Val Leu Leu Ala Leu Leu Ala Pro
 1               5                  10                  15

<210> SEQ ID NO 4
<211> LENGTH: 24
<212> TYPE: PRT
<213> ORGANISM: Artificial Sequence
<220> FEATURE:
<223> OTHER INFORMATION: syntetically generated peptide
<221> NAME/KEY: VARIANT
<222> LOCATION: 1
<223> OTHER INFORMATION: Xaa = Glu, Asp, or Lys
<221> NAME/KEY: VARIANT
<222> LOCATION: 2
<223> OTHER INFORMATION: Xaa = Lys, Glu, Ala, or Asn
<221> NAME/KEY: VARIANT
<222> LOCATION: 5
<223> OTHER INFORMATION: Xaa = Glu, Lys, or Ile
<221> NAME/KEY: VARIANT
<222> LOCATION: 6
<223> OTHER INFORMATION: Xaa = Arg, Lys, or Asp
<221> NAME/KEY: VARIANT
<222> LOCATION: 7
<223> OTHER INFORMATION: Xaa = Asp or Glu
<221> NAME/KEY: VARIANT
<222> LOCATION: (8)...(8)
<223> OTHER INFORMATION: Xaa = Asp, Val, Ser, Gly, or Glu
<221> NAME/KEY: VARIANT
<222> LOCATION: (13)...(13)
<223> OTHER INFORMATION: Xaa = Glu, Lys, or Asp

```
<221> NAME/KEY: VARIANT
<222> LOCATION: (15)...(15)
<223> OTHER INFORMATION: Xaa = Arg, Lys, or Gln
<221> NAME/KEY: VARIANT
<222> LOCATION: (16)...(16)
<223> OTHER INFORMATION: Xaa = Glu, His, Lys, or Leu
<221> NAME/KEY: VARIANT
<222> LOCATION: (19)...(19)
<223> OTHER INFORMATION: Xaa = Glu, Asp, Asn, Ala, or Val
<221> NAME/KEY: VARIANT
<222> LOCATION: (20)...(20)
<223> OTHER INFORMATION: Xaa = Lys, Asp, Gln, Asn, Thr, or Met
<221> NAME/KEY: VARIANT
<222> LOCATION: (21)...(21)
<223> OTHER INFORMATION: Xaa = Lys, Asp, Glu, Gly, or Asn
<221> NAME/KEY: VARIANT
<222> LOCATION: (22)...(22)
<223> OTHER INFORMATION: Xaa = Thr, Glu, Gly, or Lys
<221> NAME/KEY: VARIANT
<222> LOCATION: (23)...(23)
<223> OTHER INFORMATION: Xaa = Gly, Ala, Glu, Gln, Lys, or Asp
<221> NAME/KEY: VARIANT
<222> LOCATION: (24)...(24)
<223> OTHER INFORMATION: Xaa = Val, Ile, Asp, or Gly

<400> SEQUENCE: 4

Xaa Xaa Leu Gly Xaa Xaa Xaa Xaa Thr Ile Pro Pro Xaa Tyr Xaa Xaa
 1               5                  10                  15

Leu Leu Xaa Xaa Xaa Xaa Xaa Xaa
            20

<210> SEQ ID NO 5
<211> LENGTH: 5
<212> TYPE: PRT
<213> ORGANISM: Artificial Sequence
<220> FEATURE:
<223> OTHER INFORMATION: syntetically generated peptide

<400> SEQUENCE: 5

Ser Phe Leu Leu Arg
 1               5

<210> SEQ ID NO 6
<211> LENGTH: 16
<212> TYPE: PRT
<213> ORGANISM: Drosophila melanogaster

<400> SEQUENCE: 6

Arg Gln Ile Lys Ile Trp Phe Gln Asn Arg Arg Met Lys Trp Lys Lys
 1               5                  10                  15

<210> SEQ ID NO 7
<211> LENGTH: 4
<212> TYPE: PRT
<213> ORGANISM: Artificial Sequence
<220> FEATURE:
<223> OTHER INFORMATION: synthetically generated peptide

<400> SEQUENCE: 7

Leu Leu Val Tyr
 1

<210> SEQ ID NO 8
<211> LENGTH: 24
<212> TYPE: PRT
<213> ORGANISM: Homo sapiens

<400> SEQUENCE: 8

Glu Glu Leu Gly Lys Arg Glu Val Thr Ile Pro Pro Lys Tyr Arg Glu
```

```
                1               5              10              15

Leu Leu Glu Lys Lys Glu Gly Ile
            20

<210> SEQ ID NO 9
<211> LENGTH: 24
<212> TYPE: PRT
<213> ORGANISM: Bos taurus

<400> SEQUENCE: 9

Glu Glu Leu Gly Lys Arg Glu Ser Thr Pro Pro Lys Tyr Lys Glu
 1               5              10                      15

Leu Leu Asn Lys Glu Glu Gly Ile
            20

<210> SEQ ID NO 10
<211> LENGTH: 24
<212> TYPE: PRT
<213> ORGANISM: Sus scrofa

<400> SEQUENCE: 10

Glu Glu Leu Gly Lys Arg Glu Val Thr Leu Pro Pro Lys Tyr Arg Glu
 1               5              10                      15

Leu Leu Asp Lys Lys Glu Gly Ile
            20

<210> SEQ ID NO 11
<211> LENGTH: 24
<212> TYPE: PRT
<213> ORGANISM: Oryctolagus cuniculus

<400> SEQUENCE: 11

Glu Glu Leu Gly Lys Arg Glu Val Thr Ile Pro Pro Lys Tyr Arg Glu
 1               5              10                      15

Leu Leu Glu Lys Lys Thr Gly Val
            20

<210> SEQ ID NO 12
<211> LENGTH: 24
<212> TYPE: PRT
<213> ORGANISM: Rattus norvegicus

<400> SEQUENCE: 12

Glu Ala Leu Gly Ile Lys Glu Gly Thr Ile Pro Pro Glu Tyr Arg Lys
 1               5              10                      15

Leu Leu Glu Lys Asn Glu Ala Ile
            20

<210> SEQ ID NO 13
<211> LENGTH: 24
<212> TYPE: PRT
<213> ORGANISM: Homo sapiens

<400> SEQUENCE: 13

Asp Lys Leu Gly Glu Arg Asp Asp Thr Ile Pro Pro Glu Tyr Arg His
 1               5              10                      15

Leu Leu Asp Asp Asn Gly Gln Asp
            20

<210> SEQ ID NO 14
<211> LENGTH: 24
<212> TYPE: PRT
```

<213> ORGANISM: Bos taurus

<400> SEQUENCE: 14

Asp Lys Leu Gly Glu Arg Asp Asp Thr Ile Pro Pro Lys Tyr Gln His
 1               5                  10                  15

Leu Leu Asp Asp Asn Lys Glu Gly
            20

<210> SEQ ID NO 15
<211> LENGTH: 24
<212> TYPE: PRT
<213> ORGANISM: Sus scrofa

<400> SEQUENCE: 15

Asp Lys Leu Gly Glu Arg Asp Asp Thr Ile Pro Pro Glu Tyr Arg His
 1               5                  10                  15

Leu Leu Asp Lys Asp Glu Glu Gly
            20

<210> SEQ ID NO 16
<211> LENGTH: 24
<212> TYPE: PRT
<213> ORGANISM: Oryctolagus cuniculus

<400> SEQUENCE: 16

Asp Lys Leu Gly Glu Arg Asp Asp Thr Ile Pro Pro Glu Tyr Arg His
 1               5                  10                  15

Leu Leu Asp Gln Gly Glu Gln Asp
            20

<210> SEQ ID NO 17
<211> LENGTH: 24
<212> TYPE: PRT
<213> ORGANISM: Rattus norvegicus

<400> SEQUENCE: 17

Glu Lys Leu Gly Glu Arg Asp Asp Thr Ile Pro Pro Glu Tyr Arg His
 1               5                  10                  15

Leu Leu Asp Asn Asp Gly Lys Asp
            20

<210> SEQ ID NO 18
<211> LENGTH: 160
<212> TYPE: DNA
<213> ORGANISM: Artificial Sequence
<220> FEATURE:
<223> OTHER INFORMATION: synthetically generated oligonucleotide

<400> SEQUENCE: 18
gactagtggg cccgccgcca tggccgcggt agcgctgctc ccggcggtcc tgctggcctt     60
gctggcgccc gaaaagctgg gtgagagaga cgacacaatt cctccagagt acagggaact    120
tctggagaaa aaaacagggg tttaataggt tgcggccgcg                          160

<210> SEQ ID NO 19
<211> LENGTH: 160
<212> TYPE: DNA
<213> ORGANISM: Artificial Sequence
<220> FEATURE:
<223> OTHER INFORMATION: synthetically generated oligonucleotide

<400> SEQUENCE: 19
cgcggccgca acctattaaa ccctgttttt tttctccaga agttccctgt actctggagg     60

```
aattgtgtcg tctctctcac ccagctttc gggcgccagc aaggccagca ggaccgccgg    120
gagcagcgct accgcggcca tgcggcggg cccactagtc                          160
```

<210> SEQ ID NO 20
<211> LENGTH: 132
<212> TYPE: DNA
<213> ORGANISM: Eukaryote
<220> FEATURE:
<221> NAME/KEY: CDS
<222> LOCATION: (7)...(129)

<400> SEQUENCE: 20

```
gccgcc atg gcc gcg gta gcg ctg ctc ccg gcg gtc ctg ctg gcc ttg       48
       Met Ala Ala Val Ala Leu Leu Pro Ala Val Leu Leu Ala Leu
       1               5                   10 ctg gcg ccc gaa aag ctg ggt gag aga gac gac aca att cct cca gag      96
Leu Ala Pro Glu Lys Leu Gly Glu Arg Asp Asp Thr Ile Pro Pro Glu
15                  20                  25                  30 tac agg gaa ctt ctg gag aaa aaa aca ggg gtt tga                     132
Tyr Arg Glu Leu Leu Glu Lys Lys Thr Gly Val
                35                  40
```

<210> SEQ ID NO 21
<211> LENGTH: 41
<212> TYPE: PRT
<213> ORGANISM: Eukaryote

<400> SEQUENCE: 21

```
Met Ala Ala Val Ala Leu Leu Pro Ala Val Leu Leu Ala Leu Leu Ala
1               5                   10                  15

Pro Glu Lys Leu Gly Glu Arg Asp Asp Thr Ile Pro Pro Glu Tyr Arg
                20                  25                  30

Glu Leu Leu Glu Lys Lys Thr Gly Val
                35                  40
```

<210> SEQ ID NO 22
<211> LENGTH: 132
<212> TYPE: DNA
<213> ORGANISM: Eukaryote
<220> FEATURE:
<221> NAME/KEY: CDS
<222> LOCATION: (7)...(129)

<400> SEQUENCE: 22

```
gccgcc atg gcc gcg gta gcg ctg ctc ccg gcg gtc ctg ctg gcc ttg       48
       Met Ala Ala Val Ala Leu Leu Pro Ala Val Leu Leu Ala Leu
       1               5                   10 ctg gcg ccc gag gaa ttg ggt aaa aga gaa gtc aca att cct cca aaa      96
Leu Ala Pro Glu Glu Leu Gly Lys Arg Glu Val Thr Ile Pro Pro Lys
15                  20                  25                  30 tat agg gaa cta ttg gct aaa aag gaa ggg atc tga                     132
Tyr Arg Glu Leu Leu Ala Lys Lys Glu Gly Ile
                35                  40
```

<210> SEQ ID NO 23
<211> LENGTH: 41
<212> TYPE: PRT
<213> ORGANISM: Eukaryote

<400> SEQUENCE: 23

```
Met Ala Ala Val Ala Leu Leu Pro Ala Val Leu Leu Ala Leu Leu Ala
1               5                   10                  15
```

```
                                            -continued
Pro Glu Glu Leu Gly Lys Arg Glu Val Thr Ile Pro Pro Lys Tyr Arg
            20                  25                  30

Glu Leu Leu Ala Lys Lys Glu Gly Ile
        35                  40
```